(12) United States Patent
Patel et al.

(10) Patent No.: US 9,663,621 B2
(45) Date of Patent: May 30, 2017

(54) MOISTURE CURABLE COMPOSITIONS

(71) Applicant: MOMENTIVE PERFORMANCE MATERIALS INC., Waterford, NY (US)

(72) Inventors: Mihirkumar Maheshbhai Patel, Bangalore (IN); Anantharaman Dhanabalan, Bangalore (IN)

(73) Assignee: MOMENTIVE PERFORMANCE MATERIALS INC., Waterford, NY (US)

(*) Notice: Subject to any disclaimer, the term of this patent is extended or adjusted under 35 U.S.C. 154(b) by 0 days.

(21) Appl. No.: 14/913,769

(22) PCT Filed: Aug. 18, 2014

(86) PCT No.: PCT/US2014/051405
§ 371 (c)(1),
(2) Date: Feb. 23, 2016

(87) PCT Pub. No.: WO2015/026687
PCT Pub. Date: Feb. 26, 2015

(65) Prior Publication Data
US 2016/0200875 A1 Jul. 14, 2016

Related U.S. Application Data

(60) Provisional application No. 61/869,202, filed on Aug. 23, 2013.

(51) Int. Cl.
| | | |
|---|---|---|
| *C08G 77/08* | (2006.01) | |
| *C07C 277/00* | (2006.01) | |
| *C07F 7/08* | (2006.01) | |
| *C08G 77/38* | (2006.01) | |
| *C08G 77/388* | (2006.01) | |
| *C08K 5/54* | (2006.01) | |
| *C08G 59/40* | (2006.01) | |
| *C07C 279/04* | (2006.01) | |
| *C08G 77/442* | (2006.01) | |
| *C08L 101/10* | (2006.01) | |

(52) U.S. Cl.
CPC ............ *C08G 77/08* (2013.01); *C07C 277/00* (2013.01); *C07C 279/04* (2013.01); *C07F 7/0854* (2013.01); *C08G 59/40* (2013.01); *C08G 77/38* (2013.01); *C08G 77/388* (2013.01); *C08G 77/442* (2013.01); *C08K 5/54* (2013.01); *C08L 101/10* (2013.01); *C07C 2103/68* (2013.01)

(58) Field of Classification Search
None
See application file for complete search history.

(56) References Cited

U.S. PATENT DOCUMENTS

| | | | |
|---|---|---|---|
| 1,737,192 A | | 11/1929 | Heyn et al. |
| 3,627,722 A | | 12/1971 | Seiter |
| 3,632,557 A | | 1/1972 | Brode et al. |
| 3,668,183 A | * | 6/1972 | Hoy ................. C08G 73/028 528/228 |
| 3,786,081 A | | 1/1974 | Oppenlaender |
| 3,971,751 A | | 7/1976 | Isayama et al. |
| 4,180,642 A | * | 12/1979 | Takago ................. C08K 5/54 428/429 |
| 4,248,992 A | * | 2/1981 | Takago ................ C07F 7/0892 106/18.32 |
| 4,248,993 A | | 2/1981 | Takago |
| 4,345,053 A | | 8/1982 | Rizk et al. |
| 4,481,367 A | | 11/1984 | Knopf |
| 4,515,932 A | * | 5/1985 | Chung ................. C08G 77/08 528/12 |
| 4,520,075 A | | 5/1985 | Igarashi et al. |
| 4,625,012 A | | 11/1986 | Rizk et al. |
| 4,769,412 A | | 9/1988 | Inoue et al. |
| 4,897,335 A | * | 1/1990 | Kakimi ................ G03F 7/0285 430/138 |
| 4,954,598 A | | 9/1990 | Baghdachi et al. |
| 4,985,491 A | | 1/1991 | Reisch |
| 5,214,208 A | * | 5/1993 | Tanaka ............... G03G 9/09775 430/108.21 |
| 5,623,044 A | | 4/1997 | Chiao |
| 5,728,879 A | * | 3/1998 | Tsukahara ................ B41M 5/30 430/203 |
| 5,852,137 A | | 12/1998 | Hsieh et al. |

(Continued)

OTHER PUBLICATIONS

Yoshio, Iwakura et al, "A Synthesis of Polyguanidines by Poly Addition Reaction of Biscarbodiimides with Diamines", J. Polym Sci. Part B Polymer Letters, vol. 5, 1967, pp. 821-825.
Zhang, Xingmin et al., "Heterobimetallic dianionic guanidinate complexes of lanthanide and lithium: highly efficient precatalysts for catalytic addition of amines to carbodiimides to synthesize guanidines", Tetrahedron, vol. 67, 2011, pp. 8790-8799.
Patent Cooperation Treaty (PCT), International Search Report and Written Opinion for Application PCT/US2014/51405 filed Aug. 18, 2014, mailed Nov. 28, 2014, International Searching Authority, US.
Dardonville, et al., "Bisguanidine, bis(2-aminoimidasoline) and polyamine derivatives as potent and selective chemotherapeutic agents against Trypanosoma brucei rhodesiense. Sythesis and in vitro evaluation," Journal of Vledicinal Chemistry, vol. 47, No. 9, pp. 2296-2307. (2004).

*Primary Examiner* — Robert S Loewe
(74) *Attorney, Agent, or Firm* — Joseph Waters; McDonald Hopkins LLC

(57) ABSTRACT

The present invention provides curable compositions comprising non-tin metal accelerators that accelerate the condensation curing of moisture-curable silicones/non-silicones. In particular, the present invention provides an accelerator comprising guanidine-containing compounds that are particularly suitable as replacements for organotin in sealant and RTV formulations. Further, the compositions employing a guanidine-containing compound is comparable or superior to organotin such as DBTDL, exhibits certain behavior in the presence of components that allow for tuning or adjusting the cure characteristics of the compositions, and provides good adhesion and storage stability.

32 Claims, No Drawings

(56) References Cited

U.S. PATENT DOCUMENTS

| | | | |
|---|---|---|---|
| 5,919,888 A | 7/1999 | Lawrey et al. | |
| 6,197,912 B1 | 3/2001 | Huang et al. | |
| 6,207,794 B1 | 3/2001 | Yamasaki et al. | |
| 6,303,731 B1 | 10/2001 | Carlson et al. | |
| 6,310,170 B1 | 10/2001 | Johnston et al. | |
| 6,359,101 B1 | 3/2002 | O'Connor et al. | |
| 6,515,164 B1 | 2/2003 | Bolte et al. | |
| 6,740,725 B2* | 5/2004 | Horikoshi | C08L 83/14 525/477 |
| 6,833,423 B2 | 12/2004 | Roesler et al. | |
| 7,569,653 B2 | 8/2009 | Landon | |
| 7,741,010 B2 | 6/2010 | Taguchi | |
| 7,960,459 B2 | 6/2011 | Noro et al. | |
| 2002/0198352 A1 | 12/2002 | Tanaka et al. | |
| 2004/0122253 A1 | 6/2004 | Smith et al. | |
| 2005/0014894 A1* | 1/2005 | Flannigan | C08L 83/04 524/864 |
| 2005/0020706 A1 | 1/2005 | Kollbach et al. | |
| 2006/0272107 A1* | 12/2006 | Malle | A61Q 5/04 8/405 |
| 2008/0039565 A1 | 2/2008 | Ridley et al. | |
| 2011/0046299 A1* | 2/2011 | Maliverney | C07F 7/0854 524/588 |
| 2011/0098392 A1* | 4/2011 | Barrandon | C07C 279/04 524/403 |
| 2011/0237723 A1 | 9/2011 | Yano et al. | |
| 2011/0281969 A1 | 11/2011 | Maliverney | |
| 2012/0065308 A1* | 3/2012 | Sumi | C08L 83/04 524/139 |
| 2012/0172471 A1 | 7/2012 | Maliverney | |
| 2012/0172473 A1 | 7/2012 | Maliverney | |
| 2013/0061905 A1* | 3/2013 | Gaud | C09D 5/006 136/244 |

OTHER PUBLICATIONS

Neidlein, et al., "N-Acylcarbodiimide," Archly Der Pharmazie, vol. 299, No. 8., pp. 709-714. (1966).

* cited by examiner

MOISTURE CURABLE COMPOSITIONS

CROSS REFERENCE TO RELATED APPLICATIONS

The present application claims priority to and the benefit of PCT Application No. PCT/US2014/051405, entitled "Moisture Curable Compositions," filed on Aug. 18, 2014, which claims priority to and the benefit of U.S. Provisional Patent Application No. 61/869,202, entitled "Moisture Curable Compositions" filed on Aug. 23, 2013, the disclosure of each of which is incorporated herein by reference in its entirety.

FIELD

The present invention relates to curable compositions comprising silyl-terminated curable polymers and a non-toxic condensation accelerator based on a guanidine-containing compound. In particular, the present invention provides curable compositions comprising guanidine-containing compounds as alternatives to organotin catalysts.

BACKGROUND

Polymers having reactive terminal silyl groups or compositions comprising such polymers can be hydrolyzed and condensed in the presence of water and metal catalysts. Suitable known catalysts for curable compositions include compounds employing metals such as Sn, Ti, Zn, or Ca. Organotin compounds such as, for example, dibutyltin dilaurate (DBTDL) are widely used as condensation cure catalysts to accelerate the moisture-assisted curing of a number of different polyorganosiloxanes and non-silicone polymers having reactive terminal silyl groups such as room temperature vulcanizing (RTV) formulations including RTV-1 and RTV-2 formulations. Environmental regulatory agencies and directives, however, have increased or are expected to increase restrictions on the use of organotin compounds in formulated products. For example, while formulations with greater than 0.5 wt. % dibutyltin presently require labeling as toxic with reproductive 1B classification, dibutyltin-containing formulations are proposed to be completely phased out in consumer applications during the next four to six years.

The use of alternative organotin compounds such as dioctyltin compounds and dimethyltin compounds can only be considered as a short-term remedial plan, as these organotin compounds may also be regulated in the future. It would be beneficial to identify non-tin-based accelerators that accelerate the condensation curing of moisture-curable silicones and non-silicones.

Substitutes for organotin catalysts should exhibit properties similar to organotin compounds in terms of curing, storage, and appearance. Non-tin accelerators would also desirably initiate the condensation reaction of the selected polymers and complete this reaction upon the surface and may be in the bulk in a desired time schedule. There are therefore many proposals for the replacement of organometallic tin compounds with other metal- and non-metal-based compounds. These new accelerators have specific advantages and disadvantages in view of replacing tin compounds perfectly. Therefore, there is still a need to address the weaknesses of possible non-tin compounds as suitable accelerators for condensation cure reactions. The physical properties of uncured and cured compositions also warrant examination, in particular to maintain the ability to adhere onto the surface of several substrates.

Prior replacement accelerators for organotin compounds generally cannot maintain their ability to cure when exposed to humidity or ambient air after storage over months in a sealed cartridge. It is always a specific requirement for moisture-curable compositions to achieve the shortest possible curing times, showing a tack-free surface as well as curing through the complete bulk in thick section for RTV-1 and RTV-2 compositions. Additionally, such compositions should provide a reasonable adhesion after cure onto a variety of substrates. Thus, there is still a need for alternative materials to replace tin as a core accelerator in moisture curable compositions.

SUMMARY

The present invention provides tin-free, curable compositions comprising silyl-terminated polymers and a non-toxic condensation accelerator based on guanidine-containing compounds. In one embodiment, the present invention provides curable compositions employing a guanidine-containing compound comprising a plurality of guanidine functional groups as a condensation accelerator. The guanidine-containing compounds can comprise two, three, four, or more guanidine functional groups.

In one embodiment, the curable composition comprises (A) a polymer having at least a reactive silyl group; (B) a crosslinker or chain extender; and (C) a condensation accelerator comprising a guanidine-containing compound comprising a plurality of guanidine functional groups. In one embodiment, the guanidine-containing is of the formula:

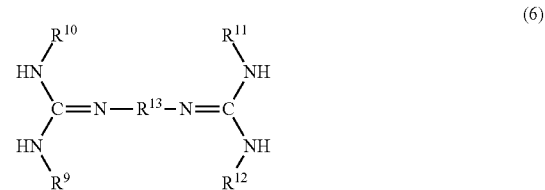

(6)

where $R^9$, $R^{10}$, $R^{11}$, and $R^{12}$ are independently chosen from an alkyl, a substituted alkyl, an alkenyl, a substituted alkenyl, an alkynyl, a substituted alkynyl, a carbocycle, a heterocycle, an aryl, or a heteroaryl; and $R^{13}$ is chosen from an alkylene, a cycloalkylene, an alkynylene, an alkenylene, an arylene, a siloxane derivative, or a polysiloxane derivative.

In another embodiment, the guanidine-containing compound is of the formula:

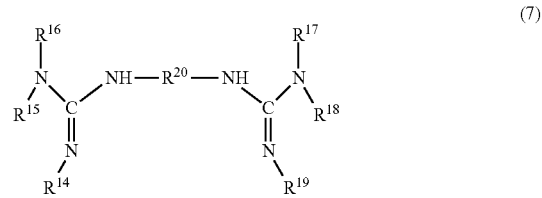

(7)

where $R^{14}$, $R^{15}$, $R^{16}$, $R^{17}$, $R^{18}$, and $R^{19}$ are independently chosen from hydrogen, an alkyl, a substituted alkyl, an alkenyl, a substituted alkenyl, an alkynyl, a substituted alkynyl, a carbocycle, a heterocycle, an aryl, or a heteroaryl;

and $R^{20}$ is chosen from an alkylene, a cycloalkylene, an alkynylene, an alkenylene, an arylene, a siloxane derivative, or a polysiloxane derivative.

In one embodiment, the curable composition comprises from about 0.0001 to about 10 parts per weight of accelerator (C) per 100 parts per weight of the polymer (A). In another embodiment, the curable composition comprises from about 0.005 to about 0.05 wt. pt. of accelerator (C) per 100 parts of the polymer (A).

In one aspect, the invention provides a curable composition exhibiting a relatively short tack-free time, curing through the bulk, as well as long storage stability in the cartridge, i.e., in the absence of humidity. Guanidine compounds comprising multiple guanidine functional groups, have been unexpectedly found to exhibit curing behavior similar to or even better than organotin compounds, and, therefore, can be suitable as replacements for organotin accelerators in compositions having a reactive, silyl-terminated polymer that can undergo condensation reactions, such as in RTV-1 and RTV-2 formulations.

Curable compositions using guanidine-containing compounds may also exhibit certain storage stability of the uncured composition in the cartridge, adhesion onto several surfaces, and a cure rate in a predictable time scheme.

In one aspect, the present invention provides a composition for forming a cured polymer composition comprising: (A) a polymer having at least one reactive silyl group; (B) a crosslinker or chain extender chosen from an alkoxysilane, an alkoxysiloxane, an oximosilane, an oximosiloxane, an enoxysilane, an enoxysiloxane, an aminosilane, an aminosiloxane, a carboxysilane, a carboxysiloxane, an alkylamidosilane, an alkylamidosiloxane, an arylamidosilane, an arylamidosiloxane, an alkoxyaminosilane, an alkoxyaminosiloxane, an alkoxycarbamatosilane, an alkoxycarbamatosiloxane, and combinations of two or more thereof; (C) an accelerator chosen from a guanidine-containing compound comprising a plurality of guanidine functional groups; (D) optionally at least one adhesion promoter chosen from a silane or siloxane other than the compounds listed under (B); (E), optionally, a filler component; and (F) at least one acidic compound chosen from a phosphate ester, a phosphonate ester, a phosphonic acid, a phosphorous acid, a phosphite, a phosphonite ester, a sulfate, a sulfite, a pseudohalogenide, a branched $C_4$-$C_{25}$ alkyl carboxylic acid, or a combination of two or more thereof.

In one embodiment, the present invention provides a curable composition that is substantially free of tin.

In one embodiment, the polymer (A) has the formula: $[R^1{}_aR^2{}_{3-a}Si-Z-]_n-X-Z-SiR^1{}_aR^2{}_{3-a}$. In another embodiment, X is chosen from a polyurethane; a polyester; a polyether; a polycarbonate; a polyolefin; a polyesterether; and a polyorganosiloxane having units of $R^3SiO_{1/2}$, $R^2SiO$, $RSiO_{3/2}$, and/or $SiO_2$, n is 0 to 100, a is 0 to 2, R, $R^1$, and $R^2$ can be identical or different at the same silicon atom and chosen from $C_1$-$C_{10}$ alkyl; $C_1$-$C_{10}$ alkyl substituted with one or more of Cl, F, N, O, or S; a phenyl; $C_7$-$C_{16}$ alkylaryl; $C_7$-$C_{16}$ arylalkyl; $C_2$-$C_{20}$-polyalkylene ether; or a combination of two or more thereof. In yet another aspect, $R^2$ is chosen from OH, $C_1$-$C_8$ alkoxy, $C_2$-$C_{18}$ alkoxyalkyl, alkoxyaryl, oximoalkyl, oximoaryl, enoxyalkyl, enoxyaryl, aminoalkyl, aminoaryl, carboxyalkyl, carboxyaryl, amidoalkyl, amidoaryl, carbamatoalkyl, carbamatoaryl, or a combination of two or more thereof, and Z is a bond, a divalent unit selected from the group of a $C_1$-$C_{14}$ alkylene, or O.

According to one embodiment, the crosslinker component (B) is chosen from tetraethylorthosilicate (TEOS); methyltrimethoxysilane (MTMS); vinyltrimethoxysilane; methylvinyldimethoxysilane; dimethyldimethoxysilane; dimethyldiethoxysilane; vinyltriethoxysilane; tetra(n-propyl) orthosilicate; tris(methylethylketoximo)vinylsilane; tris (methylethylketoximo)methylsilane; tris(acetamido) methylsilane; bis(acetamido)dimethylsilane; tris(N-methylacetamido)methylsilane; bis(N-methylacetamido) dimethylsilane; (N-methylacetamido)methyldialkoxysilane; tris(benzamido)methylsilane; tris(propenoxy)methylsilane; alkyldialkoxyamidosilanes; alkylalkoxybisamidosilanes; methylethoxybis(N-methylbenzamido)silane; methylethoxydibenzamidosilane; methyldimethoxy(ethylmethylketoximo)silane; bis(ethylmethylketoximo)methylmethoxysilane; (acetaldoximo)methyldimethoxysilane; (N-methylcarbamato)methyldimethoxysilane; (N-methylcarbamato) ethyldimethoxy silane; (isopropenoxy)methyldimethoxysilane; (isopropenoxy)trimethoxysilane; tris(isopropenoxy)methylsilane; (but-2-en-2-oxy) methyldimethoxysilane; (1-phenylethenoxy) methyldimethoxysilane; 2-((1-carboethoxy)propenoxy) methyldimethoxysilane; bis(N-methylamino) methylmethoxysilane; (N-methylamino) vinyldimethoxysilane; tetrakis(N,N-diethylamino)silane; methyldimethoxy(N-methylamino)silane; methyltris(cyclohexylamino)silane; methyldimethoxy(N-ethylamino)silane; dimethylbis(N,N-dimethylamino)silane; methyldimethoxy (N-isopropylamino)silane dimethylbis(N,N-diethylamino) silane; ethyldimethoxy(N-ethylpropionamido)silane; methyldimethoxy(N-methylacetamido)silane; methyltris(N-methylacetamido)silane; ethyldimethoxy(N-methylacetamido)silane; methyltris(N-methylbenzamido) silane; methylmethoxybis(N-methylacetamido)silane; methyldimethoxy(ε-caprolactamo)silane; trimethoxy(N-methylacetamido)silane; methyldimethoxy(O-ethylacetimidato)silane; methyldimethoxy(O-propylacetimidato)silane; methyldimethoxy(N,N',N'-trimethylureido)silane; methyldimethoxy(N-allyl-N',N'-dimethylureido)silane; methyldimethoxy(N-phenyl-N',N'-dimethylureido)silane; methyldimethoxy(isocyanato)silane; dimethoxydiisocyanatosilane; methyldimethoxyisothiocyanatosilane; methylmethoxydiisothiocyanatosilane; methyltriacetoxysilane; methylmethoxydiacetoxysilane; methylethoxydiacetoxysilane; methylisopropoxydiacetoxysilane; methyl(n-propoxy)diacetoxysilane; methyldimethoxyacetoxysilane; methyldiethoxyacetoxysilane; methyldiisopropoxyacetoxysilane; methyldi(n-propoxy)acetoxysilane; or the condensates thereof; or a combination of two or more thereof.

In one embodiment, the curable composition is free of any adhesion promoters. In another embodiment, the curable composition comprises an adhesion promoter.

According to one embodiment, the adhesion promoter component (D) is chosen from an (aminoalkyl)trialkoxysilane, an (aminoalkyl)alkyldialkoxysilane, a bis(trialkoxysilylalkyl)amine, a tris(trialkoxysilylalkyl)amine, a tris(trialkoxysilylalkyl)cyanuarate, a tris(trialkoxysilylalkyl) isocyanurate, an (epoxyalkyl)trialkoxysilane, an (epoxyalkylether)trialkoxysilane, or a combination of two or more thereof.

According to one embodiment, the component (F) is chosen from a phosphate ester of the formula: $(R^3O)PO(OH)_2$; a phosphite ester of the formula $(R^3O)P(OH)_2$; or a phosphonic acid of the formula: $R^3P(O)(OH)_2$. In another aspect, $R^3$ is a $C_1$-$C_{18}$ alkyl, a $C_2$-$C_{20}$ alkoxyalkyl, phenyl, a $C_7$-$C_{12}$ alkylaryl, a $C_2$-$C_4$ polyalkylene oxide ester or its mixtures with diesters; a branched $C_4$-$C_{14}$ alkyl carboxylic acid; or a combination of two or more thereof.

According to one embodiment, the composition comprises about 1 to about 10 wt. % of the crosslinker component (B) based on 100 wt. % of the polymer component (A).

According to one embodiment, the crosslinker component (B) is chosen from a silane or a siloxane, the silane or siloxane having two or more reactive groups that can undergo hydrolysis and/or condensation reaction with polymer (A) or on its own in the presence of water and component (F).

According to one embodiment, the polymer component (A) is chosen from a polyorganosiloxane comprising divalent units of the formula $[R^2SiO]$ in the backbone, wherein R is chosen from $C_1$-$C_{10}$ alkyl; $C_1$-$C_{10}$ alkyl substituted with one or more of Cl, F, N, O, or S; phenyl; $C_7$-$C_{16}$ alkylaryl; $C_7$-$C_{16}$ arylalkyl; $C_2$-$C_{20}$ polyalkylene ether; or a combination of two or more thereof.

According to one embodiment, the condensation accelerator (C) is present in an amount of from about 0.1 to about 7 wt. pt. per 100 wt. pt. of component (A).

According to one embodiment, the component (F) is present in an amount of from about 0.02 to about 7 wt. pt. per 100 wt. pt. of component (A).

According to one embodiment, the polymer component (A) has the formula: $R^2_{3-a}R^1_aSi-Z-[R^2SiO]_x[R^1_2SiO]_y-Z-SiR^1_aR^2_{3-a}$, whereby x is 0 to 10000; y is 0 to 1000; a is 0 to 2; R is methyl. In another aspect, $R^1$ is chosen from a $C_1$-$C_{10}$ alkyl; a $C_1$-$C_{10}$ alkyl substituted with one or more of Cl, F, N, O, or S; a phenyl; a $C_7$-$C_{16}$ alkylaryl; a $C_7$-$C_{16}$ arylalkyl; a $C_2$-$C_{20}$ polyalkylene ether; or a combination of two or more thereof, and other siloxane units may be present in amounts less than 10 mol. % preferably methyl, vinyl, phenyl. In yet another embodiment, $R^2$ is chosen from OH, a $C_1$-$C_8$ alkoxy, a $C_2$-$C_{18}$ alkoxyalkyl, an oximoalkyl, an enoxyalkyl, an aminoalkyl, a carboxyalkyl, an amidoalkyl, an amidoaryl, a carbamatoalkyl, or a combination of two or more thereof, and Z is —O—, a bond, or —$C_2H_4$—.

According to one embodiment, the composition further comprises a solvent chosen from an alkylbenzene, a trialkylphosphate, a triarylphosphate, a phthalic acid ester, an arylsulfonic acid ester having a viscosity-density constant (VDC) of at least 0.86 that is miscible with a polyorganosiloxane and accelerator component (C), a polyorganosiloxane devoid of reactive groups and having a viscosity of less than 2000 mPa·s at 25° C., or a combination of two or more thereof.

According to one embodiment, the composition is provided as a one-part composition.

According to one embodiment, the composition comprises 100 wt. % of component (A), 0.1 to about 10 wt. % of at least one crosslinker (B), 0.01 to about 7 wt. % of an accelerator (C), 0 to about 5 wt. % of an adhesion promoter (D), 0 to about 300 wt. % of component (E), 0.01 to about 8 wt. % of component (F) whereby this composition can be stored in the absence of humidity and is curable in the presence of humidity upon exposure to ambient air.

According to one embodiment, the composition is a two-part composition comprising: (i) a first portion comprising the polymer component (A), optionally the filler component (E), and optionally the acidic compound (F); and (ii) a second portion comprising the crosslinker (B), the accelerator component (C), optionally, the adhesion promoter (D), and the acidic compound (F), whereby (i) and (ii) are stored separately until applied for curing by mixing of the components (i) and (ii).

According to one embodiment, portion (i) comprises 100 wt. % of component (A), and 0 to 70 wt. pt. of component (E); and portion (ii) comprises 0.1 to 10 wt. pt. of at least one crosslinker (B), 0.01 to 7 wt. pt. of an accelerator (C), 0 to 5 pt. wt. of an adhesion promoter (D), and 0.02 to 3 pt. wt. component (F).

In another aspect, the present invention provides, a composition for forming a cured polymer composition comprising (A) a polymer having at least a reactive silyl group, where the polymer is free of siloxane bonds; (B) a crosslinker or chain extender chosen from an alkoxysilane, an alkoxysiloxane, an oximosilane, an oximosiloxane, an enoxysilane, an enoxysiloxane, an aminosilane, an aminosiloxane, a carboxysilane, a carboxysiloxane, an alkylamidosilane, an alkylamidosiloxane, an arylamidosilane, an arylamidosiloxane, an alkoxyaminosilane, an alklarylaminosiloxane, an alkoxycarbamatosilane, an alkoxycarbamatosiloxane, the condensates thereof, and combinations of two or more thereof; and (C) a condensation accelerator comprising a guanidine-containing compound comprising a plurality of guanidine functional groups.

The cure chemistry of these moisture-curable compositions can vary based upon the nature of the polymers and their moisture-curable groups. For example, alkoxysilyl groups first hydrolyze to give silanol functionalities, which then condense with the extrusion of water to give the siloxane network. Such compositions typically comprise an alkoxysilyl- or silanol-functional polymer and a crosslinking agent. Tri- and tetraalkoxysilanes are commonly used as crosslinking agents and will react with water or directly with silanol groups to crosslink the system.

In another aspect, the present invention provides a composition for forming a cured polymer composition comprising (A) a compound having at least one hydridosilyl group, and (C) a condensation accelerator comprising a guanidine-containing compound comprising a plurality of guanidine functional groups. However, for compositions comprising hydridosilyl groups or both hydridosilyl and silanol functionalities, such a crosslinking agent is not required. In fact, due to the multitude of hydridosilyl groups present, the hydridosilyl-containing compound is often referred to as the crosslinking agent. In these compositions, hydridosilyl groups may react with water to give silanol functionalities or they may react directly with silanol groups to form siloxane bonds with extrusion of hydrogen gas. For transition-metal-catalyzed compositions comprising a hydridosilyl-containing compound, inhibitors are commonly used to ensure adequate shelf life or pot life.

DETAILED DESCRIPTION

The present invention provides a curable composition employing a guanidine-containing compound as a condensation accelerator. The guanidine-containing compounds comprise a plurality of guanidine functional groups. Compositions comprising such guanidine-containing compounds exhibit good curing properties and can even exhibit similar or superior curing properties compared to compositions employing organotin compounds, such as DBTDL, in terms of accelerating moisture-assisted condensation curing of silicones to result in cross-linked silicones that can be used as sealants and RTVs (Room-Temperature Vulcanized Rubber). Further, the compositions comprising such guanidine-containing compounds also exhibit improved storage stability.

As used herein, "alkyl" includes straight, branched, and cyclic alkyl groups. Specific and non-limiting examples of alkyls include, but are not limited to, methyl, ethyl, propyl, isobutyl, ethyl-hexyl, etc.

As used herein, "substituted alkyl" includes an alkyl group that contains one or more substituent groups that are inert under the process conditions to which the compound containing these groups is subjected. The substituent groups also do not substantially interfere with the process. As used herein, unsubstituted means the particular moiety carries hydrogen atoms on its constituent atoms, e.g. $CH_3$ for unsubstituted methyl. Substituted means that the group can carry typical functional groups known in organic chemistry.

As used herein, "aryl" includes a non-limiting group of any aromatic hydrocarbon from which one hydrogen atom has been removed. An aryl may have one or more aromatic rings, which may be fused, connected by single bonds or other groups. Specific and non-limiting examples of aryls include, but are not limited to, tolyl, xylyl, phenyl, naphthalenyl, etc.

As used herein, "substituted aryl" includes an aromatic group substituted as set forth in the above definition of "substituted alkyl." Similar to an aryl, a substituted aryl may have one or more aromatic rings, which may be fused, connected by single bonds or other groups; however, when the substituted aryl has a heteroaromatic ring, the free valence in the substituted aryl group can be a heteroatom (such as nitrogen) of the heteroaromatic ring instead of a carbon. In one embodiment, substituted aryl groups herein contain 1 to about 30 carbon atoms.

As used herein, "alkenyl" includes any straight, branched, or cyclic alkenyl group containing one or more carbon-carbon double bonds, where the point of substitution can be either a carbon-carbon double bond or elsewhere in the group. Specific and non-limiting examples of alkenyls include, but are not limited to, vinyl, propenyl, allyl, methallyl, ethylidenyl norbornane, etc.

As used herein, "alkynyl" includes any straight, branched, or cyclic alkynyl group containing one or more carbon-carbon triple bonds, where the point of substitution can be either at a carbon-carbon triple bond or elsewhere in the group.

As used herein, "unsaturated" refers to one or more double or triple bonds. In one embodiment, it refers to carbon-carbon double or triple bonds.

As used herein, the terms "alkylene", "cycloalkylene", "alkynylene", "alkenylene", and "arylene" alone or as part of another substituent refers to a divalent radical derived from an alkyl, cycloalkyl, heteroalkyl, alkynyl, alkenyl, or aryl group, respectively. The respective radicals can be substituted or unsubstituted, linear or branched.

In one embodiment, the present invention provides a curable composition comprising a polymer component (A) comprising a reactive terminal silyl group; a crosslinker component (B); an accelerator component (C) comprising an guanidine-containing compound comprising a plurality of guanidine functional groups; optionally an adhesion promoter component (D); an optional filler component (E); and optionally an acidic compound (F), and optionally auxiliary components (G).

In another embodiment, the present invention provides a curable composition comprising a polymer component (A) comprising a hydridosilyl group; an accelerator component (C) comprising a guanidine-containing compound comprising a plurality of guanidine functional groups; and optionally auxiliary components (G).

The polymer component (A) may be a liquid- or solid-based polymer having a reactive terminal silyl group. The polymer component (A) is not particularly limited and may be chosen from any cross-linkable polymer as may be desired for a particular purpose or intended use. Non-limiting examples of suitable polymers for the polymer component (A) include polyorganosiloxanes (A1) or organic polymers free of siloxane bonds (A2), wherein the polymers (A1) and (A2) comprise reactive terminal silyl groups. In one embodiment, the polymer component (A) may be present in an amount of from about 10 to about 90 wt. % of the curable composition. In one embodiment, the curable composition comprises about 100 pt. wt. of the polymer component (A).

As described above, the polymer component (A) may include a wide range of polyorganosiloxanes. In one embodiment, the polymer component may comprise one or more polysiloxanes and copolymers of formula (1):

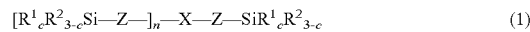

$[R^1_cR^2_{3-c}Si-Z-]_n-X-Z-SiR^1_cR^2_{3-c}$ (1)

$R^1$ may be chosen from linear or branched alkyl, linear or branched heteroalkyl, cycloalkyl, heterocycloalkyl, aryl, heteroaryl, linear or branched aralkyl, linear or branched heteroaralkyl, or a combination of two or more thereof. In one embodiment, $R^1$ may be chosen from $C_1$-$C_{10}$ alkyl; $C_1$-$C_{10}$ alkyl substituted with one or more of Cl, F, N, O, or S; phenyl; $C_7$-$C_{16}$ alkylaryl; $C_7$-$C_{16}$ arylalkyl; $C_2$-$C_{20}$ polyalkylene ether; or a combination of two or more thereof. Exemplary groups are methyl, trifluoropropyl, and/or phenyl groups.

$R^2$ may be a group reactive to protic agents such as water. Exemplary groups for $R^2$ include OH, alkoxy, alkenyloxy, alkyloximo, alkylcarboxy, arylcarboxy, alkylamido, arylamido, or a combination of two or more thereof. In one embodiment, $R^2$ is chosen from OH, $C_1$-$C_8$ alkoxy, $C_2$-$C_{18}$ alkoxyalkyl, amino, alkenyloxy, alkyloximo, alkylamino, arylamino, alkylcarboxy, arylcarboxy, alkylamido, arylamido, alkylcarbamato, arylcarbamato, or a combination of two or more thereof.

Z may be a bond, a divalent linking unit selected from the group of O, hydrocarbons which can contain one or more O, S, or N atom, guanidine-containing, urethane, ether, ester, urea units or a combination of two or more thereof. If the linking group Z is a hydrocarbon group, then Z is linked to the silicon atom over a silicon-carbon bond. In one embodiment, Z is chosen from a $C_1$-$C_{14}$ alkylene.

X is chosen from a polyurethane; a polyester; a polyether; a polycarbonate; a polyolefin; a polyesterether; and a polyorganosiloxane having units of $R^1_3SiO_{1/2}$, $R^1_2SiO$, $R^1SiO_{3/2}$, and/or $SiO_2$, where $R^1$ is defined as above. X may be a divalent or multivalent polymer unit selected from the group of siloxy units linked over oxygen or hydrocarbon groups to the terminal silyl group comprising the reactive group $R^2$ as described above, polyether, alkylene, isoalkylene, polyester, or polyurethane units linked over hydrocarbon groups to the silicon atom comprising one or more reactive groups $R^2$ as described above. The hydrocarbon group X can contain one or more heteroatoms such as N, S, O, or P forming guanidine-containings, esters, ethers, urethanes, esters, and/or ureas. In one embodiment, the average polymerization degree ($P_n$) of X should be more than 6, e.g. polyorganosiloxane units of $R^1_3SiO_{1/2}$, $R^1_2SiO$, $R^1SiO_{3/2}$, and/or $SiO_2$. In formula (2), n is 0 to 100; desirably 1, and c is 0 to 2, desirably 0 to 1.

Non-limiting examples of the components for unit X include polyoxyalkylene polymers such as polyoxyethylene, polyoxypropylene, polyoxybutylene, polyoxyethylene-polyoxypropylene copolymer, polyoxytetramethylene, or polyoxypropylene-polyoxybutylene copolymer; ethylene-propylene copolymer, polyisobutylene, polychloroprene, polyisoprene, polybutadiene, copolymer of isobutylene and isoprene, copolymers of isoprene or butadiene and acrylonitrile and/or styrene, or hydrocarbon polymers such as hydrogenated polyolefin polymers produced by hydrogenating these polyolefin polymers; polyester polymer manufactured by a condensation of dibasic acid such as adipic acid or phthalic acid and glycol, or ring-opening polymerization of lactones; polyacrylic acid ester produced by radical polymerization of a monomer such as $C_2$-$C_8$-alkyl acrylates, vinyl polymers, e.g., acrylic acid ester copolymer of acrylic acid ester such as ethyl acrylate or butyl acrylate and vinyl acetate, acrylonitrile, methyl methacrylate, acrylguanidine-containing, or styrene; graft polymer produced by polymerizing the above organic polymer with a vinyl monomer; polycarbonates; polysulfide polymer; polyguanidine-containing polymer such as Nylon 6 produced by ring-opening polymerization of ε-caprolactam, Nylon 6-6 produced by polycondensation of hexamethylenediamine and adipic acid, etc., Nylon 12 produced by ring-opening polymerization of ε-laurolactam, copolymeric polyguanidine-containings, polyurethanes, or polyureas.

Particularly suitable polymers include, but are not limited to, polysiloxanes, polyoxyalkylenes, saturated hydrocarbon polymers such as polyisobutylene, hydrogenated polybutadiene and hydrogenated polyisoprene, or polyethylene, polypropylene, polyesters, polycarbonates, polyurethanes, polyurea polymers and the like. Furthermore, saturated hydrocarbon polymer, polyoxyalkylene polymer, and vinyl copolymer are particularly suitable due to their low glass transition temperature which provide a high flexibility at low temperatures, i.e., below 0° C.

The reactive silyl groups in formula (1) can be introduced by employing silanes containing a functional group which has the ability to react by known methods with unsaturated hydrocarbons via hydrosilylation, or reaction of SiOH, aminoalkyl or -aryl, HOOC-alkyl or -aryl, HO-alkyl or -aryl, HS-alkyl or -aryl, Cl(O)C-alkyl or -aryl, epoxyalkyl or epoxycycloalkyl groups in the prepolymer to be linked to a reactive silyl group via condensation or ring-opening reactions. Examples of the main embodiments include the following: (i) siloxane prepolymers having a SiOH group that can undergo a condensation reaction with a silane (LG) $SiR^1_cR^2_{3-c}$ whereby a siloxy bond ≡Si—O—$SiR^1_cR^2_{3-c}$ is formed while the addition product of the leaving group (LG) and hydrogen is released (LG-H); (ii) silanes having an unsaturated group that is capable of reacting via hydrosilylation or radical reaction with a SiH group or radically activated groups of a silane such as SiH or an unsaturated group; and (iii) silanes including organic or inorganic prepolymers having OH, SH, amino, epoxy, —COCl, —COOH groups, which can react complementarily with epoxy, isocyanato, OH, SH, cyanato, carboxylic halogenides, reactive alkylhalogenides, lactones, lactams, or amines, that is to link the reactive prepolymer with the organofunctional silanes to yield a silyl functional polymer.

Silanes suitable for method (i) include alkoxysilanes, especially tetraalkoxysilanes, di- and trialkoxysilanes, di- and triacetoxysilanes, di- and triketoximosilanes, di- and trialkenyloxysilanes, di- and tricarbonamidosilanes, wherein the remaining residues at the silicon atom of the silane are substituted or unsubstituted hydrocarbons. Other non-limiting silanes for method (i) include alkyltrialkoxysilanes, such as vinyltrimethoxysilane, methyltrimethoxysilane, propyltrimethoxysilane, aminoalkyltrimethoxysilane, ethyltriacetoxysilane, methyl- or propyltriacetoxysilane, methyltributanonoximosilane, methyltripropenyloxysilane, methyltribenzamidosilane, or methyltriacetamidosilane. Prepolymers suitable for reaction under method (i) are SiOH-terminated polyalkylsiloxanes, which can undergo a condensation reaction with a silane having hydrolyzable groups attached to the silicon atom. Exemplary SiOH-terminated polyalkyldisiloxanes include polydimethylsiloxanes.

Suitable silanes for method (ii) include alkoxysilanes, especially trialkoxysilanes ($HSi(OR)_3$) such as trimethoxysilane, triethoxysilane, methyldiethoxysilane, methyldimethoxysilane, and phenyldimethoxysilane. Hydrogenchlorosilanes are in principle possible but are less desirable due to the additional replacement of the halogen through an alkoxy, acetoxy group, etc. Other suitable silanes include organofunctional silanes having unsaturated groups which can be activated by radicals, such as vinyl, allyl, mercaptoalkyl, or acrylic groups. Non-limiting examples include vinyltrimethoxysilane, mercaptopropyltrimethoxysilane, and methacryloxypropyltrimethoxysilane. Prepolymers suitable for reaction under method (ii) include vinyl-terminated polyalkylsiloxanes, preferably polydimethylsiloxanes, hydrocarbons with unsaturated groups which can undergo hydrosilylation or can undergo radically induced grafting reactions with a corresponding organofunctional group of a silane comprising, for example, unsaturated hydrocarbon or a SiH group.

Another method for introducing silyl groups into hydrocarbon polymers can be the copolymerization of unsaturated hydrocarbon monomers with the unsaturated groups of silanes. The introduction of unsaturated groups into a hydrocarbon prepolymer may include, for example, the use of alkenyl halogenides as chain stopper after polymerization of the silicon free hydrocarbon moiety.

Desirable reaction products between the silanes and prepolymers include the following structures: —$SiR^1_2$O—$SiR^1_2$—$CH_2$—$CH_2$—$SiR^1_cR^2_3$, or (hydrocarbon)-[Z—$SiR^1_cR^2_{3-c}]_n$. Suitable silanes for method (iii) include, but are not limited to, alkoxysilanes, especially silanes having organofunctional groups to be reactive to —OH, —SH, amino, epoxy, —COCl, or —COOH.

In one embodiment, these silanes have an isocyanatoalkyl group such as gamma-isocyanatopropyltrimethoxysilane, gamma-isocyanatopropylmethyldimethoxysilane, gamma-isocyanatopropyltriethoxysilane, gamma-glycidoxypropylethyldimethoxysilane, gamma-glycidoxypropyltrimethoxysilane, gamma-glycidoxypropyltriethoxysilane, beta-(3,4-epoxycyclohexyl)ethyltrimethoxysilane, beta-(3,4-epoxycyclohexyl)ethyltriethoxysilane, epoxylimonyltrimethoxysilane, N-(2-aminoethyl)-aminopropyltrimethoxysilane, gamma-aminopropyltriethoxysilane, gamma-aminopropyltrimethoxysilane, gamma-aminopropylmethyldimethoxysilane, gamma-aminopropylmethyldiethoxysilane, etc.

In one embodiment, it is desirable to select either blocked amines or isocyanates $(Z'—X)_n—Z'$ for carrying out first a complete mixing and then the following coupling reaction. Examples of blocking agents are disclosed in EP 0947531 and other blocking procedures that employ heterocyclic nitrogen compounds such as caprolactam or butanone oxime, or cyclic ketones referred to in U.S. Pat. No. 6,827,875 both of which are incorporated herein by reference in their entirety.

Examples of suitable prepolymers for a reaction under method (iii) include, but are not limited to, polyalkylene oxides having OH groups, in one embodiment with a high molecular weight ($M_w$, weight-average molecular weight>6000 g/mol) and a polydispersity $M_w/M_n$ of less than 1.6; urethanes having remaining NCO groups, such as NCO functionalized polyalkylene oxides, especially blocked isocyanates. Prepolymers selected from the group of hydrocarbons having —OH, —COOH, amino, epoxy groups, which can react complementarily with an epoxy, isocyanato, amino, carboxyhalogenide or halogenalkyl group of the corresponding silane having further reactive groups useful for the final cure.

Suitable isocyanates for the introduction of a NCO group into a polyether may include toluene diisocyanate, diphenylmethane diisocyanate, or xylene diisocyanate, or aliphatic polyisocyanate such as isophorone diisocyanate, or hexamethylene diisocyanate.

The polymerization degree of the unit X depends on the requirements of viscosity and mechanical properties of the cured product. If X is a polydimethylsiloxane unit, the average polymerization degree based on the number average molecular weight $M_n$ is preferably 7 to 5000 siloxy units, preferably 200 to 2000 units. In order to achieve a sufficient tensile strength of >5 MPa, an average polymerization degree $P_n$ of >250 is suitable whereby the polydimethylsiloxanes have a viscosity of more than 300 mPa·s at 25° C. If X is a hydrocarbon unit other than a polysiloxane unit, the viscosity with respect to the polymerization degree is much higher.

Examples of the method for synthesizing a polyoxyalkylene polymer include, but are not limited to, a polymerization method using an alkali catalyst such as KOH, a polymerization method using a metal-porphyrin complex catalyst such as a complex obtained by reacting an organoaluminum compound, a polymerization method using a composite metal cyanide complex catalyst disclosed, e.g., in U.S. Pat. Nos. 3,427,256; 3,427,334; 3,278,457; 3,278,458; 3,278,459; 3,427,335; 6,696,383; and 6,919,293.

If the group X is selected from hydrocarbon polymers, then polymers or copolymers having isobutylene units are particularly desirable due to its physical properties such as excellent weatherability, excellent heat resistance, and low gas and moisture permeability.

Examples of the monomers include olefins having 4 to 12 carbon atoms, vinyl ether, aromatic vinyl compound, vinylsilanes, and allylsilanes. Examples of the copolymer component include 1-butene, 2-butene, 2-methyl-1-butene, 3-methyl-1-butene, pentene, 4-methyl-1-pentene, hexene, vinylcyclohexene, methyl vinyl ether, ethyl vinyl ether, isobutyl vinyl ether, styrene, alpha-methylstyrene, dimethylstyrene, beta-pinene, indene, and for example, but not limited to, vinyltrialkoxysilanes, e.g. vinyltrimethoxysilane, vinylmethyldichlorosilane, vinyldimethylmethoxysilane, divinyldichlorosilane, divinyldimethoxysilane, allyltrichlorosilane, allylmethyldichlorosilane, allyldimethylmethoxysilane, diallyldichlorosilane, diallyldimethoxysilane, gamma-methacryloyloxypropyltrimethoxysilane, and gamma-methacryloyloxypropylmethyldimethoxysilane.

Examples of suitable siloxane-free organic polymers include, but are not limited to, silylated polyurethane (SPUR), silylated polyester, silylated polyether, silylated polycarbonate, silylated polyolefins like polyethylene, polypropylene, silylated polyesterether and combinations of two or more thereof. The siloxane-free organic polymer may be present in an amount of from about 10 to about 90 wt. % of the composition or about 100 pt. wt.

In one embodiment, the polymer component (A) may be silylated polyurethane (SPUR). Such moisture curable compounds are known in the art in general and can be obtained by various methods including (i) reacting an isocyanate-terminated polyurethane (PUR) prepolymer with a suitable silane, e.g., one possessing both hydrolyzable functionality at the silicon atom, such as, alkoxy, etc., and secondly active hydrogen-containing functionality such as mercaptan, primary or secondary amine, preferably the latter, etc., or by (ii) reacting a hydroxyl-terminated PUR (polyurethane) prepolymer with a suitable isocyanate-terminated silane, e.g., one possessing one to three alkoxy groups. The details of these reactions, and those for preparing the isocyanate-terminated and hydroxyl-terminated PUR prepolymers employed therein can be found in, amongst others: U.S. Pat. Nos. 4,985,491; 5,919,888; 6,207,794; 6,303,731; 6,359,101; and 6,515,164, and published U.S. Patent Publication Nos. 2004/0122253 and US 2005/0020706 (isocyanate-terminated PUR prepolymers); U.S. Pat. Nos. 3,786,081 and 4,481,367 (hydroxyl-terminated PUR prepolymers); U.S. Pat. Nos. 3,627,722; 3,632,557; 3,971,751; 5,623,044; 5,852,137; 6,197,912; and 6,310,170 (moisture-curable SPUR (silane modified/terminated polyurethane) obtained from reaction of isocyanate-terminated PUR prepolymer and reactive silane, e.g., aminoalkoxysilane); and, U.S. Pat. Nos. 4,345,053; 4,625,012; 6,833,423; and published U.S. Patent Publication 2002/0198352 (moisture-curable SPUR obtained from reaction of hydroxyl-terminated PUR prepolymer and isocyanatosilane). The entire contents of the foregoing U.S. patent documents are incorporated by reference herein. Other examples of moisture-curable SPUR materials include those described in U.S. Pat. No. 7,569,653, the disclosure of which is incorporated by reference in its entirety.

In one embodiment, the polymer component (A) may be a polymer of formula (2):

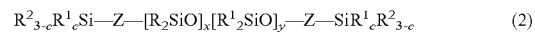

$$R^2{}_{3-c}R^1{}_cSi{-}Z{-}[R_2SiO]_x[R^1{}_2SiO]_y{-}Z{-}SiR^1{}_cR^2{}_{3-c} \quad (2)$$

where $R^1$, $R^2$, Z, and c are defined as above with respect to formula (2); R is $C_1$-$C_6$ alkyl (an exemplary alkyl being methyl); x is 0 to about 10,000, in one embodiment from 11 to about 2500; and y is 0 to about 10,000; preferably 0 to 500. In one embodiment, Z in a compound of formula (2) is a bond or a divalent $C_1$-$C_{14}$ alkylene group, especially preferred is —$C_2H_4$—.

In one embodiment, the polymer component (A) may be a polyorganosiloxane of the formula (3):

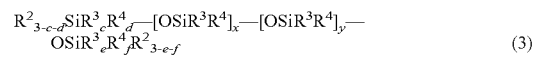

$$R^2{}_{3-c-d}SiR^3{}_cR^4{}_d{-}[OSiR^3R^4]_x{-}[OSiR^3R^4]_y{-}OSiR^3{}_eR^4{}_fR^2{}_{3-e-f} \quad (3)$$

$R^3$ and $R^4$ can be identical or different on the same silicon atom and are chosen from hydrogen; $C_1$-$C_{10}$ alkyl; $C_1$-$C_{10}$ heteroalkyl; $C_3$-$C_{12}$ cycloalkyl; $C_2$-$C_{30}$ heterocycloalkyl; $C_6$-$C_{13}$ aryl; $C_7$-$C_{30}$ alkylaryl; $C_7$-$C_{30}$ arylalkyl; $C_4$-$C_{12}$ heteroaryl; $C_5$-$C_{30}$ heteroarylalkyl; $C_5$-$C_{30}$ heteroalkylaryl; $C_2$-$C_{100}$ polyalkylene ether; or a combination of two or more thereof. $R^2$, c, x, and y are as defined above; d is 0, 1, or 2; e is 0, 1, or 2; and f is 0, 1, or 2.

Non-limiting examples of suitable polysiloxane-containing polymers (A1) include, for example, silanol-stopped polydimethylsiloxane, silanol or alkoxy-stopped polyorganosiloxanes, e.g., methoxystopped polydimethylsiloxane, alkoxy-stopped polydimethylsiloxane-polydiphenylsiloxane copolymer, and silanol or alkoxy-stopped fluoroalkyl-substituted siloxanes such as poly(methyl 3,3,3-trifluoropropyl) siloxane and poly(methyl 3,3,3-trifluoropropyl)siloxane-polydimethyl siloxane copolymer. The polyorganosiloxane component (A1) may be present in an amount of about 10 to about 90 wt. % of the composition or 100 pt. wt. In one preferred embodiment, the polyorganosiloxane component has an average chain length in the range of about 10 to about 2500 siloxy units, and the viscosity is in the range of about 10 to about 500,000 mPa·s at 25° C.

Alternatively, the composition may include silyl-terminated organic polymers (A2) that are free of siloxane units, and which undergo curing by a condensation reaction comparable to that of siloxane containing polymers (A1). Similar to the polyorganosiloxane polymer (A1), the organic polymers (A2) that are suitable as the polymer component (A) include a terminal silyl group. In one embodiment, the terminal silyl group may be of the formula (4):

where $R^1$, $R^2$, and d are as defined above.

The polysiloxane composition may further include a crosslinker or a chain extender as component (B). In one embodiment, the crosslinker is of the formula (5):

wherein $R^1$, $R^2$, and d are as defined above. Alternatively, the crosslinker component may be a condensation product of formula (5) wherein one or more but not all $R^2$ groups are hydrolyzed and released in the presence of water and then intermediate silanols undergo a condensation reaction to give a Si—O—Si bond and water. The average polymerization degree can result in a compound having 2 to 10 Si units.

In one embodiment, the crosslinker is an alkoxysilane having a formula $R^3_d(R^1O)_{4-d}Si$, wherein $R^1$, $R^3$, and d are defined as above. In another embodiment, the crosslinker is an acetoxysilane having a formula $(R^3_d(R^1CO_2)_{4-d}Si$, wherein $R^1$, $R^3$, and d are defined as above. In still another embodiment, the crosslinker is an oximosilane having a formula $R^3_d(R^1R^4C\!=\!N\!-\!O)_{4-d}Si$, where $R^1$, $R^3$, $R^4$, and d are defined as above.

As used herein, the term crosslinker includes a compound including an additional reactive component having at least two hydrolysable groups and less than three silicon atoms per molecule not defined under (A). In one embodiment, the crosslinker or chain extender may be chosen from an alkoxysilane, an alkoxysiloxane, an oximosilane, an oximosiloxane, an enoxysilane, an enoxysiloxane, an aminosilane, an aminosiloxane, a carboxysilane, a carboxysiloxane, an alkylamidosilane, an alkylamidosiloxane, an arylamidosilane, an arylamidosiloxane, an alkoxyaminosilane, an alkylarylaminosiloxane, an alkoxycarbamatosilane, an alkoxycarbamatosiloxane, an imidatosilane, a ureidosilane, an isocyanatosilane, a isothiocyanatosilane, the condensates thereof, a hydridosilane, a hydridosiloxane (organosiloxane monomer, oligomer and/or polymer having, per molecule, at least one reactive ≡SiH unit), and combinations of two or more thereof. Examples of suitable cross-linkers include, but are not limited to, tetraethylorthosilicate (TEOS); methyltrimethoxysilane (MTMS); methyltriethoxysilane; vinyltrimethoxysilane; vinyltriethoxysilane; methylphenyldimethoxysilane; 3,3,3-trifluoropropyltrimethoxysilane; methyltriacetoxysilane; vinyltriacetoxysilane; ethyltriacetoxysilane; di-butoxydiacetoxysilane; phenyltripropionoxysilane; methyltris(methylethylketoximo)silane; vinyltris(methylethylketoximo)silane; 3,3,3-trifluoropropyltris(methylethylketoximo)silane; methyltris(isopropenoxy)silane; vinyltris(isopropenoxy)silane; ethylpolysilicate; dimethyltetraacetoxydisiloxane; tetra-n-propylorthosilicate; methyldimethoxy(ethylmethylketoximo)silane; methylmethoxybis(ethylmethylketoximo)silane; methyldimethoxy(acetaldoximo)silane; methyldimethoxy(N-methylcarbamato)silane; ethyldimethoxy(N-methylcarbamato)silane; methyldimethoxyisopropenoxysilane; trimethoxyisopropenoxysilane; methyltriisopropenoxysilane; methyldimethoxy(but-2-en-2-oxy)silane; methyldimethoxy(1-phenylethenoxy)silane; methyldimethoxy-2-(1-carboethoxypropenoxy)silane; methylmethoxydi(N-methylamino)silane; vinyldimethoxy(methylamino)silane; tetra-N,N-diethylaminosilane; methyldimethoxy(methylamino)silane; methyltri(cyclohexylamino)silane; methyldimethoxy(ethylamino)silane; dimethyldi(N,N-dimethylamino)silane; methyldimethoxy(isopropylamino)silane; dimethyldi(N,N-diethylamino)silane; ethyldimethoxy(N-ethylpropionamido)silane; methyldimethoxy(N-methylacetamido)silane; methyltris(N-methylacetamido)silane; ethyldimethoxy(N-methylacetamido) silane; methyltris(N-methylbenzamido)silane; methylmethoxybis(N-methylacetamido)silane; methyldimethoxy(caprolactamo)silane; trimethoxy(N-methylacetamido)silane; methyldimethoxy(ethylacetimidato)silane; methyldimethoxy(propylacetimidato)silane; methyldimethoxy(N,N',N'-trimethylureido)silane; methyldimethoxy(N-allyl-N',N'-dimethylureido)silane; methyldimethoxy(N-phenyl-N',N'-dimethylureido)silane; methyldimethoxyisocyanatosilane; dimethoxydiisocyanatosilane; methyldimethoxyisothiocyanatosilane; methylmethoxydiisothiocyanatosilane, the condensates thereof, or combinations of two or more thereof. In one embodiment, the crosslinker may be present in an amount from about 1 to about 10 wt. % of the composition or from about 0.1 to about 10 pt. wt. per 100 pt. wt. of the polymer component (A). In another embodiment, the crosslinker may be present in an amount from about 0.1 to about 5 pt. wt. per 100 pt. wt. of the polymer component (A). In still another embodiment, the crosslinker may be present in an amount from about 0.5 to about 3 pt. wt. per 100 pt. wt. of the polymer component (A). Here as elsewhere in the specification and claims, numerical values may be combined to form new or undisclosed ranges.

Additional alkoxysilanes in an amount greater than 0.1 wt. % of component (A) that are not consumed by the reaction between the prepolymer Z'—X—Z' and which comprise additional functional groups selected from $R^5$ can also work as an adhesion promoter and are defined and counted under component (D).

In one embodiment, the condensation accelerator (C) comprises a compound comprising a plurality of guanidine functional groups. The guanidine-containing compounds can comprise two, three, four, or more guanidine functional groups. The inventors have found that such compounds can accelerate the curing of compositions comprising compounds with a reactive silyl group. The guanidine-containing compounds can, in one embodiment, even be considered a catalyst in such compositions.

The guanidine compounds generally comprise a plurality of guanidine groups attached to a linking group. The guanidine groups can be attached to the linking group through the imine nitrogen atom or an amine nitrogen atom of the guanidine group.

In one embodiment, the condensation accelerator (C) comprises a guanidine-containing compound of the Formula (6):

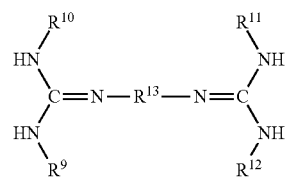

where $R^9$, $R^{10}$, $R^{11}$, and $R^{12}$ are independently chosen from an alkyl, a substituted alkyl, an alkenyl, a substituted alkenyl, an alkynyl, a substituted alkynyl, a carbocycle, a heterocycle, an aryl, or a heteroaryl; and $R^{13}$ is chosen from an alkylene, a cycloalkylene, an alkynylene, an alkenylene, an arylene, a siloxane derivative, or a polysiloxane derivative.

In another embodiment, the condensation accelerator (C) comprises a guanidine-containing compound of the Formula (7):

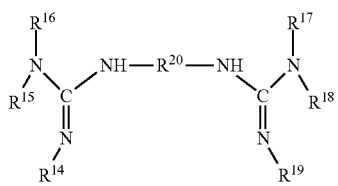

(7)

where $R^{14}$, $R^{15}$, $R^{16}$, $R^{17}$, $R^{18}$, and $R^{19}$ are independently chosen from hydrogen, an alkyl, a substituted alkyl, an alkenyl, a substituted alkenyl, an alkynyl, a substituted alkynyl, a carbocycle, a heterocycle, an aryl, or a heteroaryl; and $R^{20}$ is chosen from an alkylene, a cycloalkylene, an alkynylene, an alkenylene, an arylene, a siloxane derivative, or a polysiloxane derivative.

In one embodiment, $R^9$-$R^{12}$ and $R^{14}$-$R^{19}$ are independently chosen from substituted or unsubstituted, branched or straight chain $C_1$-$C_{30}$ alkyl; substituted or unsubstituted, branched or straight chain $C_2$-$C_{18}$ alkenyl; substituted or unsubstituted, branched or straight chain $C_2$-$C_{18}$ alkynyl; —(OCH$_2$CH$_2$)$_{1-15}$OH; —(OC$_3$H$_6$)$_{1-15}$OH; substituted or unsubstituted, saturated or unsaturated, carbocycles or heterocycles; or substituted or unsubstituted aryl or heteroaryl. In one embodiment, $R^9$-$R^{12}$ and $R^{14}$-$R^{19}$ are substituted or unsubstituted, branched or straight chain $C_1$-$C_9$ alkyl; substituted or unsubstituted, branched or straight chain $C_2$-$C_9$ alkenyl; substituted or unsubstituted, branched or straight chain $C_2$-$C_9$ alkynyl; —(OCH$_2$CH$_2$)$_{1-7}$—R; —(OC$_3$H$_6$)$_{1-7}$—R; substituted or unsubstituted, branched or straight chain $C_1$-$C_5$ alkyl; substituted or unsubstituted, branched or straight chain $C_2$-$C_5$ alkenyl; substituted or unsubstituted, branched or straight chain $C_2$-$C_5$ alkynyl; substituted or unsubstituted, saturated or unsaturated, carbocycles or heterocycles; or substituted or unsubstituted aryl or heteroaryl.

In one embodiment, $R^9$-$R^{12}$ and $R^{14}$-$R^{19}$ are independently chosen from substituted or unsubstituted, branched or straight chain $C_1$-$C_5$ alkyl; substituted or unsubstituted, branched or straight chain $C_2$-$C_5$ alkenyl; substituted or unsubstituted, branched or straight chain $C_2$-$C_5$ alkynyl; substituted or unsubstituted, saturated or unsaturated, carbocycle or heterocycle selected from cyclopropyl, cyclobutyl, cyclopentyl, cyclohexyl, pyrrolidinyl, piperidyl, imidazolidinyl, pyrazolidinyl, pyrazolinyl, piperazinyl, morpholinyl, chromanyl, indolinyl, and the like, including their corresponding iso-forms; or a substituted or unsubstituted fused or unfused aryl or heteroaryl selected from phenyl, benzyl, naphthyl, furyl, benzofuranyl, pyranyl, pyrazinyl, thienyl, pyrrolyl, imidazolyl, pyridyl, pyrimidinyl, pyridazinyl, indolyl, indolizinyl, indoazolyl, purinyl, quinolyl, thiazolyl, phthalazinyl, quinoxalinyl, quinazolinyl, benzothienyl, anthryl, phenathtryl, and the like, including their corresponding iso-forms.

In one embodiment, $R^9$-$R^{12}$ and $R^{14}$-$R^{19}$ are independently chosen from are methyl, ethyl, propyl, isopropyl, butyl, isobutyl, tert-butyl, 2-ethyl-hexyl, cyclopentyl, cyclohexyl, phenyl, pyridinyl, or pyrrolidinyl.

Non-limiting examples of suitable divalent linking groups for $R^{13}$ and $R^{20}$ include a straight-chain, branched or cyclic alkylene group such as an alylene group having 1 to 30 carbon atoms, 1 to 12 carbon atoms, and even 1 to 4 carbon atoms (e.g., methylene, ethylene, propylene, butylene, pentylene, hexylene, octylene, and decylene), an aralkylene group such as an aralkylene group having 7 to 30 carbon atoms, even 7 to 13 carbon atoms (e.g., benzylidene and cinnamylidene), an arylene group such as an arylene group having 6 to 30 carbon atoms, even 6 to 15 carbon atoms (e.g., phenylene, cumenylene, mesitylene, tolylene, and xylylene). The divalent radical groups can include substitutents such as cyclic groups or fused cyclic structures. In one embodiment, the $R^{13}$ and/or $R^{20}$ group can include a fused ring system, a ring with a bridge group, a fused ring system where at least one ring includes a bridge group. For example, the cyclic group can include 6-12 membered bicyclic cycloalkyl groups or 6-12 membered bicyclic cycloalkyl groups where at least one of the cycloalkyl groups is a bridged bicyclic group.

In one embodiment, $R^{13}$ or $R^{20}$ can comprise a siloxane derivative. The siloxane derivative can include a linear or cyclic siloxane with an alkylene group attached to the terminal Si atoms or a combination of one or more thereof. In one embodiment, the $R^{13}$ or $R^{20}$ group is a siloxane-containing group of the formula:

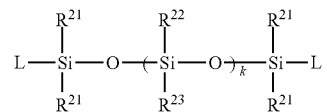

where $R^{21}$, $R^{22}$, and $R^{23}$ can be identical or different at the same silicon atom and chosen from $C_1$-$C_{10}$ alkyl; $C_1$-$C_{10}$ alkyl substituted with one or more of Cl, F, N, O, or S; a phenyl; $C_7$-$C_{16}$ alkylaryl; $C_7$-$C_{16}$ arylalkyl; $C_2$-$C_{20}$-polyalkylene ether; or a combination of two or more thereof. In yet another aspect, $R^{22}$ and $R^{23}$ are chosen from OH, $C_1$-$C_8$ alkoxy, $C_2$-$C_{18}$ alkoxyalkyl, alkoxyaryl, oximoalkyl, oximoaryl, enoxyalkyl, enoxyaryl, aminoalkyl, aminoaryl, carboxyalkyl, carboxyaryl, amidoalkyl, amidoaryl, carbamatoalkyl, carbamatoaryl, or a combination of two or more thereof, and L is a bond, a divalent unit selected from the group of a $C_1$-$C_{14}$ alkylene, or O, and k can vary from 0 to 1000. In one embodiment, k is from 0 to 100, 1-20, even 5-15. In one embodiment, L is chosen from a $C_1$-$C_{10}$ alkylene, k is from 0-20, and $R^{21}$, $R^{22}$, and $R^{23}$ are independently chosen from a $C_1$-$C_{10}$ alkyl. In one embodiment, $R^{21}$, $R^{22}$, and $R^{23}$ are each methyl.

In one embodiment, the guanidine-containing compound is of the formula:

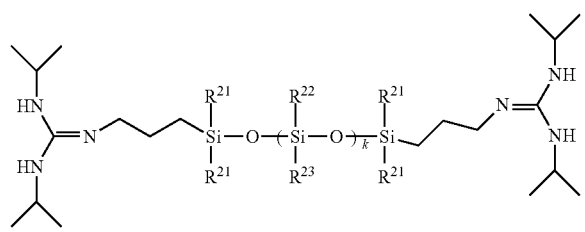

where $R^{21}$, $R^{22}$, and $R^{23}$ can be as described above.

The $R^9$-$R^{20}$ groups just discussed may themselves be unsubstituted or substituted. The alkyl, alkene, alkyne groups, etc., as indicated, may be straight chains or branched structures. For unsaturated moieties, e.g., alkenes, alkynes, unsaturated carbocycles, or unsaturated heterocycles, the degree of unsaturation may vary from one unsaturation to the maximum possible within the particular moiety. Unsaturated groups may also have a mixture of double and triple bonds.

In one embodiment, the guanidine-containing compound is of the formula:

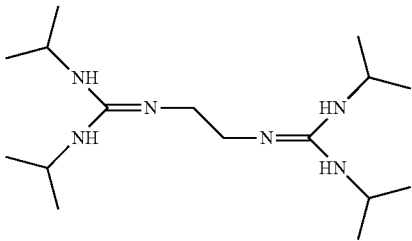 [SMILES: CC(C)NC(=NCCN=C(NC(C)C)NC(C)C)NC(C)C]

In one embodiment, the guanidine-containing compound is of the formula:

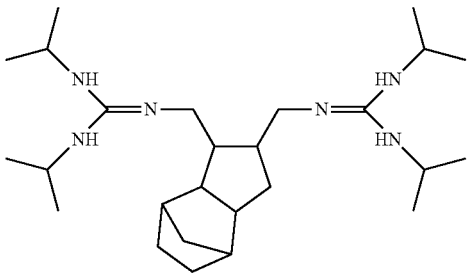 [SMILES: CC(C)NC(=NCC1CC2C3CCC(C3)C2C1CN=C(NC(C)C)NC(C)C)NC(C)C]

In one embodiment, the guanidine-containing compound is a compound of the formula:

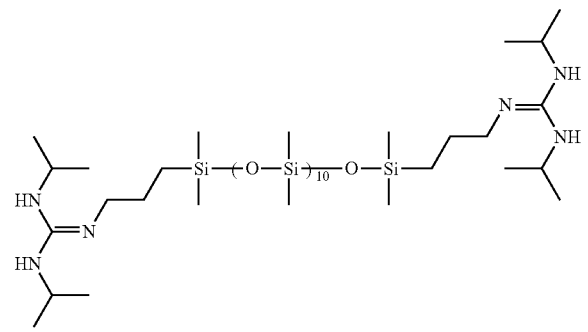

The guanidine-containing compounds can be prepared by any suitable process or reaction for preparing such compounds. One method of synthesizing bis-guanidines is described in Tetrahedron 67 (2011), 8790-8799, and includes reacting carbodiimide and an amine in the presence of a catalyst. In one embodiment, guanidine-containing containing compounds of the Formula (6) can be prepared by reacting two moles of carbodiimide with a diamine. Non-limiting examples of suitable carbodiimides include, but are not limited to N,N'-dialkylcarbodiimide such as, for example, diisopropylcarbodiimide (DIC).

In one embodiment, the present invention provides a method of making a guanidine-containing compound by reacting carbodiimide with a diamine at a temperature of from about from about 40° C. to about 70° C. for about 48 hours, where the reaction is conducted in the absence of a catalyst. A single type of carbodiimide or different carbodiimides can be used in the reaction provided the carbodiimide is provided in a total molar ratio necessary to provide the desired number of guanidine groups. The carbodiimide is provided in a molar concentration such that there is at least one mole of carbodiimide for every amine functional group in the starting amine compound. For example, two moles of carbodiimide are reacted with a diamine, three moles of carbodiimide are reacted with a triamine, etc.

In one embodiment, the present invention provides a method of forming a guanidine-containing compound comprising the reaction two moles of a carbodiimide of the formula $R^9$—N=C=N—$R^{10}$ with one mole of a diamine of the formula $NH_2$—$R^{13}$—$NH_2$, at a temperature of from about 40° C. to about 70° C. for at least 48 hours.

In another embodiment, the present invention comprises reacting one mole of a carbodiimide of the formula $R^9$—N=C=N—$R^{10}$ and one mole of a carbodiimide of the formula $R^{11}$—N=C=N—$R^{12}$ with one mole of a diamine of the formula $NH_2$—$R^{13}$—$NH_2$ at a temperature of from about 40° C. to about 70° C. for at least 48 hours.

In providing the guanidine-containing compounds in this manner, the guanidine-containing compounds do not need to be further processed or purified to remove the catalyst from the guanidine-containing compounds. This provides a guanidine-containing material that is substantially free of a metal. As used herein, the guanidine containing material is substantially free of a metal if it comprises 1 ppm or less of a metal; 0.5 ppm or less of a metal; even 0.1 ppm or less of a metal. In one embodiment, a guanidine containing material is substantially free of a metal if it comprises from about 0.1 ppm to about 1 ppm of a metal.

The accelerator (C) can include other compounds known to accelerate or catalyze the condensation reaction such as complexes or salts of metals including, but not limited to, titanium, zirconium, zinc, aluminum, iron, cobalt, strontium, bismuth; carboxylic acids including but not limited to acetic acid, lauric acid, stearic acid, and versatic acid; alkyl- and arylsulfonic acids including, but not limited to, p-toluenesulfonic acid and methanesulfonic acid; inorganic acids including, but not limited to, hydrochloric acid, phosphoric acid, and boric acid; amines including, but not limited to, trioctylamine; guanidines including but not limited to tetramethylguanidine; amidines including, but not limited to, 1,8-diazabicyclo[5.4.0]-7-undecene (DBU) and 1,5-diazabicyclo[4.3.0]non-5-ene (DBN); and inorganic bases including, but not limited to, lithium hydroxide and sodium methoxide; such that the system is substantially free of fluorine and tin.

In one embodiment, the condensation accelerator (C) can be added to the curable composition such that the guanidine-containing compound is present or added in an amount of from about 0.0001 to about 10 pt. wt. related to 100 part per weight of component (A); from about 0.001 to about 7 pt. wt. per 100 pt. wt. of component (A); from about 0.01 to about 5 pt. wt. per 100 pt. wt. of component (A); from about 0.1 to about 2.5 pt. wt. per 100 pt. wt. of component (A). In still another embodiment, the guanidine-containing compound can be added to the curable composition in an amount of from about 0.005 to about 7.0 pt. wt.; 0.01 to about 7.0 pt. wt.; about 0.05 to about 5 pt. wt.; from about 0.1 to 2.5 pt. wt.; from about 0.5 to about 2 pt. wt.; even from about 1 to about 1.5 pt. wt. per 100 parts per weight of the polymer (A). In another embodiment, the guanidine-containing compound is present in an amount of from about 0.005 to about 0.05 pt. wt. per 100 pt. wt. of component (A). Here, as elsewhere in the specification and claims, numerical values can be combined to form new and non-disclosed ranges. An increase in the amount of guanidine-containing compound as an accelerator may increase the cure rate of curing the surface and decrease the cure time for a tack-free surface and the complete cure through the bulk.

The composition optionally includes an adhesion promoter component (D) that is different from component (A) or (B). In one embodiment, the curable composition does not include an adhesion promoter. It has been found that the guanidine-containing compounds can promote curing of the composition even in the absence of an adhesion promoter. In another embodiment, the curable compositions comprise an adhesion promoter. The guanidine-containing compounds comprising a plurality of guanidine functional groups can be used with a wide range of adhesion promoters.

In one embodiment, the adhesion promoter (D) may be an organofunctional silane comprising the group $R^5$, e.g., aminosilanes, and other silanes that are not identical to the silanes of component (B), or are present in an amount that exceeds the amount of silanes necessary for endcapping the polymer (A). The amount of non-reacted silane (B) or (D) in the reaction for making (A) can be defined in that after the endcapping reaction the free silanes are evaporated at a higher temperature up to 200° C. and vacuum up to 1 mbar to be more than 0.1 wt. % of (A).

Thus, some selected amines can advantageously be added to fine tune the rate of the metal-complex-catalyzed condensation curing of silicone/non-silicone polymer containing reactive silyl groups, as desired.

In one embodiment, the composition comprises an adhesion promoter (D) comprising a group $R^5$ as described by the general formula (8):

$$R^5_g R^1_d Si(R^2)_{4-d-g} \quad (8)$$

where $R^5$ is $E\text{-}(CR^3_2)_h\text{---}W\text{---}(CH_2)_h\text{---}$; $R^1$, $R^2$, and d are as described above; g is 1 or 2; d+g=1 to 2; and h is 0 to 8, and may be identical or different.

Non-limiting examples of suitable compounds include:

$$E^1\text{-}(CR^3_2)_h\text{---}W\text{---}(CH_2)_h\text{---}SiR^1_d(R^2)_{3-d} \quad (8a) \text{ or } (8d)$$

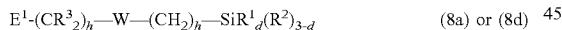

$$E^2\text{-}[(CR^3_2)_h\text{---}W\text{---}(CH_2)_h\text{---}SiR^1_d(R^2)_{3-d}]_j \quad (8b) \text{ or } (8f)$$

where j is 2 to 3.

The group E may be selected from either a group $E^1$ or $E^2$. $E^1$ may be selected from a monovalent group comprising amine, —$NH_2$, —NHR, —$(NHC_2H_5)_a$NHR, $NHC_6H_5$, halogen, pseudohalogen, unsaturated aliphatic group with up to 14 carbon atoms, epoxy-group-containing aliphatic group with up to 14 carbon atoms, cyanurate-containing group, and an isocyanurate-containing group.

$E^2$ may be selected from a group comprising a di- or multivalent group consisting of amine, polyamine, cyanurate-containing, and an isocyanurate-containing group, sulfide, sulfate, phosphate, phosphite, and a polyorganosiloxane group, which can contain $R^5$ and $R^2$ groups; W is selected from the group consisting of a single bond, a heteroatomic group selected from —COO—, —O—, epoxy, —S—, —CONH—, —HN—CO—NH— units; $R^3$ is as defined above, $R^1$ may be identical or different as defined above, $R^2$ is defined as above and may be identical or different.

Non-limiting examples of component (D) include:

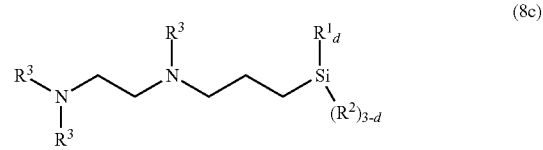
(8c)

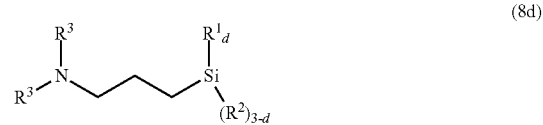
(8d)

(8e)

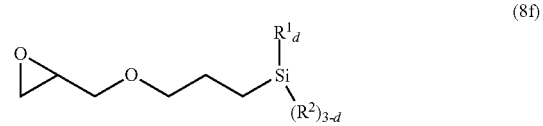
(8f)

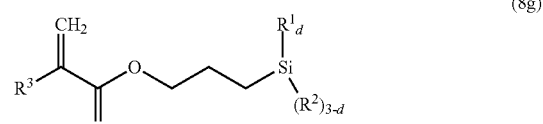
(8g)

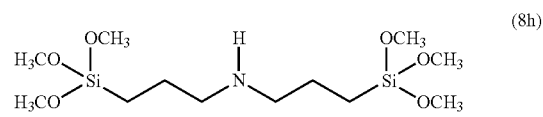
(8h)

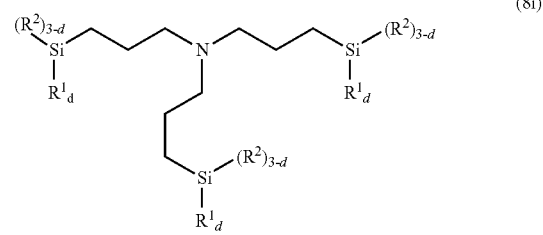
(8i)

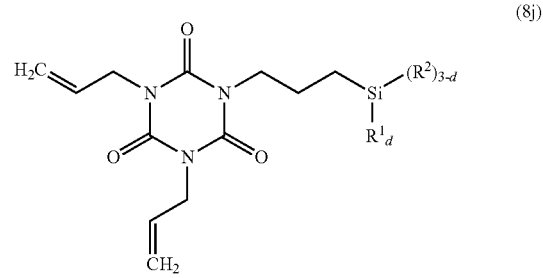
(8j)

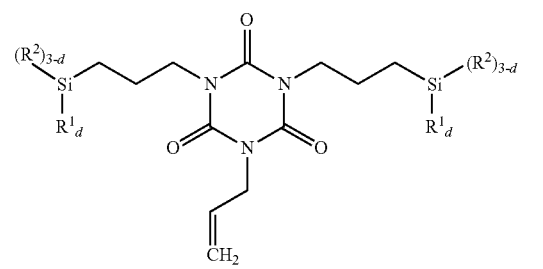
(8k)

-continued (8l)

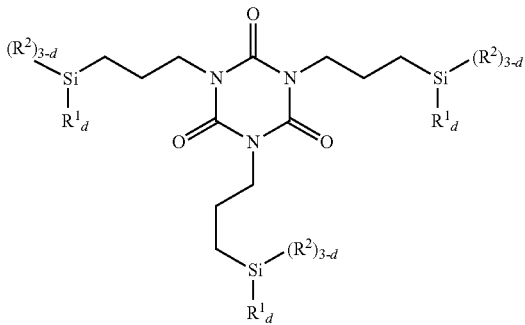

wherein $R^1$, $R^2$, and d are as defined above. Examples of component (D) include compounds of the formulas (8a-8l). Furthermore the formula (8b) of compounds (D) shall comprise compounds of the formula (8m):

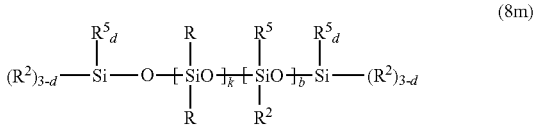

(8m)

wherein: R, $R^2$, $R^5$, and d are as defined above; k is 0 to 6 (and in one embodiment desirably 0); b is as described above (in one embodiment desirably 0 to 5); and $1+b \leq 10$. In one embodiment, $R^5$ is selected from:

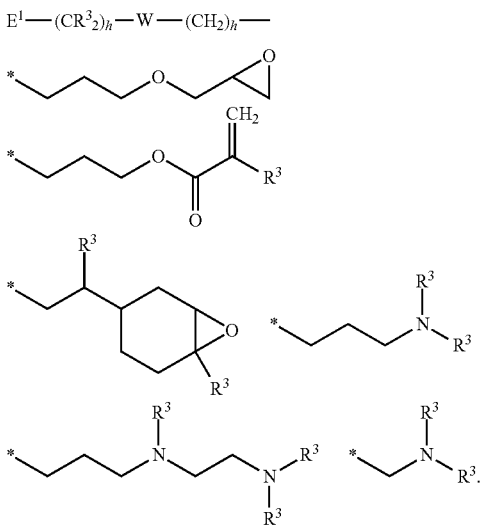

An exemplary group of adhesion promoters are selected from the group that consists of amino-group-containing silane coupling agents. The amino-group-containing silane adhesion promoter agent (D) is an acidic compound having a group containing a silicon atom bonded to a hydrolyzable group (hereinafter referred to as a hydrolyzable group attached to the silicon atom) and an amino group. Specific examples thereof include the same silyl groups with hydrolyzable groups described above. Among these groups, the methoxy group and ethoxy group are particularly suitable.

The number of the hydrolyzable groups may be 2 or more, and particularly suitable are compounds having 3 or more hydrolyzable groups.

Examples of other suitable adhesion promoter (D) include, but are not limited to N-(2-aminoethyl)aminopropyltrimethoxysilane, gamma-aminopropyltriethoxysilane, gamma-aminopropyltrimethoxysilane, bis(3-trimethoxysilypropyl)amine, N-phenyl-gamma-aminopropyltrimethoxysilane, triaminofunctionaltrimethoxysilane, gamma-aminopropylmethyldimethoxysilane, gamma-aminopropylmethyldiethoxysilane, methacryloxypropyltrimethoxysilane, methylaminopropyltrimethoxysilane, gamma-glycidoxypropylethyldimethoxysilane, gamma-glycidoxypropyltrimethoxysilane, gamma-glycidoxyethyltrimethoxysilane, gamma-glycidoxypropylmethyldimethoxysilane, gamma-glycidoxypropylmethyldiethoxysilane, beta-(3,4-epoxycyclohexyl)ethyltrimethoxysilane, beta-(3,4-epoxycyclohexyl)ethylmethyldimethoxysilane, beta-(3,4-epoxycyclohexyl)ethyltriethoxysilane, beta-(3,4-epoxycyclohexyl)ethylmethyldiethoxysilane, epoxylimonyltrimethoxysilane, isocyanatopropyltriethoxysilane, isocyanatopropyltrimethoxysilane, isocyanatopropylmethyldimethoxysilane, beta-cyanoethyltrimethoxysilane, gamma-acryloxypropyltrimethoxysilane, gamma-methacryloxypropylmethyldimethoxysilane, alpha, omega-bis(aminoalkyldiethoxysilyl)polydimethylsiloxanes (Pn=1-7), alpha, omega-bis(aminoalkyldiethoxysilyl)octamethyltetrasiloxane, 4-amino-3,3-dimethylbutyltrimethoxysilane, and N-ethyl-3-trimethoxysilyl-2-methylpropanamine, 3-(N,N-diethylaminopropyl)trimethoxysilane combinations of two or more thereof, and the like. Particularly suitable adhesion promoters include bis(alkyltrialkoxysilyl)amines and tris(alkyltrialkoxysilyl)amines including, but not limited to, bis(3-trimethoxysilylpropyl)amine and tris(3-trimethoxysilylpropyl)amine.

Also it is possible to use derivatives obtained by modifying them, for example, amino-modified silyl polymer, silylated amino polymer, unsaturated aminosilane complex, phenylamino long-chain alkyl silane and aminosilylated silicone. These amino-group-containing silane coupling agents may be used alone, or two or more kinds of them may be used in combination.

The adhesion promoter (D) may be present in an amount of from about 0.1 to about 5.0 wt. % based on 100 parts of the polymer component (A). In one embodiment, the adhesion promoter may be present in an amount of from about 0.15 to about 2.0 wt. % based on 100 parts of the polymer component (A). In another embodiment, the adhesion promoter may be present in an amount of from about 0.5 to about 1.5 wt. % of the polymer component (A). This defines the amount of (D) in composition of (A) wherein the content of free silanes coming from the endcapping of polymer (A) is smaller than 0.1 wt. %.

The present compositions may further include a filler component (E). The filler component(s) (E) may have different functions, such as to be used as reinforcing or semi-reinforcing filler, i.e., to achieve higher tensile strength after curing. The filler component may also have the ability to increase viscosity, establish pseudoplasticity/shear thinning, and demonstrate thixotropic behavior. Non-reinforcing fillers may act as volume extenders. The reinforcing fillers are characterized by having a specific surface area of more than 50 $m^2$/g related BET-surface, whereby the semi-reinforcing fillers have a specific surface area in the range of 10-50 $m^2$/g. So-called extending fillers have preferably a specific surface area of less than 10 m²/g according to the BET-method and an average particle diameter below 100 μm. In one embodiment, the semi-reinforcing filler is a calcium carbonate filler, a silica filler, or a mixture thereof. Examples of suitable reinforcing fillers include, but are not limited to, fumed silicas or precipitated silicas, which can be partially or completely treated with organosilanes or siloxanes to make them less hydrophilic and decrease the water content or control the viscosity and storage stability of the composition. These fillers are named hydrophobic fillers. Tradenames are Aerosil®, HDK®, Cab-O-Sil® etc.

Examples of suitable extending fillers include, but are not limited to, ground silicas (Celite™), precipitated and colloidal calcium carbonates (which are optionally treated with compounds such as stearate or stearic acid); reinforcing silicas such as fumed silicas, precipitated silicas, silica gels and hydrophobized silicas and silica gels; crushed and ground quartz, cristobalite, alumina, aluminum hydroxide, titanium dioxide, zinc oxide, diatomaceous earth, iron oxide, carbon black, powdered thermoplastics such as acrylonitrile, polyethylene, polypropylene, polytetrafluoroethylene and graphite or clays such as kaolin, bentonite or montmorillonite (treated/untreated), and the like.

The type and amount of filler added depends upon the desired physical properties for the cured silicone/non-silicone composition. As such, the filler may be a single species or a mixture of two or more species. The extending fillers can be present from about 0 to about 300 wt. % of the composition related to 100 parts of component (A). The reinforcing fillers can be present from about 5 to about 60 wt. % of the composition related to 100 parts of component (A), preferably 5 to 30 wt. %.

The inventive compositions optionally comprise an acidic compound (F), which, in conjunction with the adhesion promoter and guanidine-containing accelerator, may accelerate curing (as compared to curing in the absence of such compounds). The component (F) may be present in an amount of from about 0.01 to about 5 wt. % of the composition. In another embodiment 0.01 to about 8 parts per weight (pt. wt.) per 100 pt. wt. of component (A) are used, more preferably 0.02 to 3 pt. wt. per 100 pt. wt. of component (A) and most preferably 0.02 to 1 pt. wt. per 100 pt. wt. of component (A) are used.

The acidic compounds (F) may be chosen from various phosphate esters, phosphonates, phosphites, phosphonites, sulfites, sulfates, pseudohalogenides, branched alkyl carboxylic acids, combinations of two or more thereof, and the like. Without being bound to any particular theory, the acidic compounds (F) may, in one embodiment, be useful as stabilizers in order to ensure a longer storage time when sealed in a cartridge before use in contact with ambient air. Especially alkoxy-terminated polysiloxanes can lose the ability to cure after storage in a cartridge and show decreased hardness under curing conditions. It may, therefore be useful to add compounds of the formula (9), which can extend storage time or ability to cure over months.

$$O=P(OR^6)_{3-c}(OH)_c \quad (9)$$

whereby c is as defined above; and $R^6$ is selected from the group of linear or branched and optionally substituted $C_1$-$C_{30}$ alkyl groups, linear or branched $C_5$-$C_{14}$ cycloalkyl groups, $C_6$-$C_{14}$ aryl groups, $C_6$-$C_{31}$ alkylaryl groups, linear or branched $C_2$-$C_{30}$ alkenyl groups or linear or branched $C_1$-$C_{30}$ alkoxyalkyl groups, $C_4$-$C_{300}$ polyalkenylene oxide groups (polyethers), such as Marlophor® N5 acid, triorganylsilyl- and diorganyl ($C_1$-$C_8$)-alkoxysilyl groups. The phosphates can include also mixtures of primary and secondary esters. Non-limiting examples of suitable phosphonates include 1-hydroxyethane-(1,1-diphosphonic acid) (HEDP), aminotris(methylene phosphonic acid) (ATMP), diethylenetriaminepenta(methylene phosphonic acid) (DTPMP), 1,2-diaminoethane-tetra(methylene phosphonic acid) (EDTMP), and phosphonobutanetricarboxylic acid (PBTC).

In another embodiment, a compound of the formula  may be present or added where g is 1 or 2, and $R^7$ is defined as $R^6$ or di- or mulitvalent hydrocarbons with one or more amino group.

Another type are phosphonic acid compounds of the formula $R^6P(O)(OH)_2$ such as alkyl phosphonic acids preferably hexyl or octyl phosphonic acid.

In one embodiment, the acidic compound may be chosen from a mono ester of phosphoric acid of the formula $(R^8O)PO(OH)_2$; a phosphonic acid of the formula $R^8P(O)(OH)_2$; or a monoester of phosphorous acid of the formula $(R^8O)P(OH)_2$ where $R^8$ is a $C_1$-$C_{18}$ alkyl, a $C_2$-$C_{20}$ alkoxyalkyl, phenyl, a $C_7$-$C_{12}$ alkylaryl, a $C_2$-$C_4$ polyalkylene oxide ester or its mixtures with diesters, etc.

In another embodiment, the acidic compound is a branched $C_4$-$C_{30}$ alkyl carboxylic acids, including $C_5$-$C_{19}$ acids with an alpha tertiary carbon, or a combination of two or more thereof. Examples of such suitable compounds include, but are not limited to, Versatic™ Acid, lauric acid, and stearic acid. In one embodiment, the acidic compound may be a mixture comprising branched alkyl carboxylic acids. In one embodiment, the acidic compound is a mixture of mainly tertiary aliphatic $C_{10}$ carboxylic acids.

Generally, the acidic component (F) is added in a molar ratio of less than or equal to 1 with respect to accelerator (C). In embodiments, the acidic component (F) is added in a molar ratio of (F):(C) of 1:15 to 1:1.

The curable composition may also include auxiliary substances (G) such as plasticizers, pigments, stabilizers, antimicrobial agents, fungicides, biocides, and/or solvents. Preferred plasticizers for reactive polyorganosiloxanes (A) are selected from the group of polyorganosiloxanes having chain lengths of 10 to 300 siloxy units. Preferred are trimethylsilyl terminated polydimethylsiloxanes having a viscosity of 100 to 1000 mPa·s at 25° C. The choice of optional solvents (dispersion media or extenders) may have a role in assuring uniform dispersion of the accelerator, thereby altering curing speed. Such solvents include polar and non-polar solvents such as toluene, hexane, chloroform, methanol, ethanol, isopropyl alcohol, acetone, methylethyl ketone, dimethylformguanidine-containing (DMF), dimethyl sulfoxide (DMSO), N-methylpyrrolidinone (NMP), and propylene carbonate. Water can be an additional component (G) to accelerate fast curing 2-part compositions RTV-2, whereby the water can be in one part of the 2 compositions. Particularly suitable non-polar solvents include, but are not limited to, toluene, hexane, and the like if the solvents should evaporate after cure and application. In another embodiment, the solvents include high-boiling hydrocarbons such as alkylbenzenes, phthalic acid esters, arylsulfonic acid esters, trialkyl- or triarylphosphate esters, which have a low vapor pressure and can extend the volume providing lower costs. Examples cited by reference may be those of U.S. Pat. No. 6,599,633; U.S. Pat. No. 4,312,801. The solvent can be present in an amount of from about 20 to about 99 wt. % of the accelerator composition.

Applicants have found that using guanidine-containing compounds comprising a plurality of guanidine functional groups as an accelerator may provide a curable composition that yields a cured polymer exhibiting a tack-free time, hardness, and/or cure time comparable to compositions made using tin catalysts. Further, this can be achieved with or without the use of an adhesion promoter. The curing properties can be controlled by using the guanidine-containing compound with one or more adhesion promoters.

In one embodiment, a composition in accordance with the present invention comprises: 100 wt. % polymer component (A); about 0.1 to about 10 wt. % crosslinker component (B); and about 0.01 to about 7 wt. % accelerator (C). In one embodiment, the composition further comprises from about 0.1 to about 5 wt. %, in one embodiment 0.15 to 1 wt. %, of an adhesion promoter component (D); about 0 to about 300 pt. wt. filler component (E); about 0.01 to about 7 wt. % of acidic compound (F); optionally 0 to about 15 wt. % component (G), where the wt. % of components (B)-(G) are each based on 100 parts of the polymer component (A). In one embodiment, the composition comprises the component (F) in an amount of from about 0.01 to about 1 wt. % per 100 pt. wt. of component (A). In still another embodiment, the composition comprises the accelerator (C) in an amount of from about 0.1 to about 0.8 wt. % per 100 wt. % of component (A).

It will be appreciated that the curable compositions may be provided as either a one-part composition or a two-part composition. A one-part composition refers to a composition comprising a mixture of the various components described above. A two-part composition may comprise a first portion and a second portion that are separately stored and subsequently mixed together just prior to application for curing. In one embodiment, a two-part composition comprises a first portion (P1) comprising a polymer component (A) and a crosslinker component (B), and a second portion (P2) comprising the accelerator component (C) comprising the guanidine-containing compound. The first and second portions may include other components (F) and/or (G) as may be desired for a particular purpose or intended use. In one embodiment, the first portion (P1) may optionally comprise an adhesion promoter (D) and/or a filler (E), and the second portion (P2) may optionally comprise auxiliary substances (G), a cure rate modifying component (F), and water (G).

In one embodiment, a two-part composition comprises (i) a first portion comprising the polymer component (A), optionally the filler component (E), and optionally the acidic compound (F); and (ii) a second portion comprising the crosslinker (B), the accelerator component (C), optionally the adhesive promoter (D), and optionally the acidic compound (F), where portions (i) and (ii) are stored separately until applied for curing by mixing of the components (i) and (ii).

An exemplary two-part composition comprises: a first portion (i) comprising 100 pt. wt. of component (A), and 0 to 70 pt. wt. of component (E); and a second portion (ii) comprising 0.1 to 5 pt. wt. of at least one crosslinker (B); 0.01 to 4 pt. wt. of an accelerator (C); 0.1 to 2 pt. wt. of an adhesion promoter (D); and 0.02 to 1 pt. wt. component (F).

The curable compositions may be used in a wide range of applications including as materials for sealing, mold making, glazing, prototyping; as adhesives; as coatings in sanitary rooms; as joint seal between different materials, e.g., sealants between ceramic or mineral surfaces and thermoplastics; as paper release; as impregnation materials; and the like. A curable composition in accordance with the present invention comprising a guanidine-containing compound as an accelerator may be suitable for a wide variety of applications such as, for example, a general purpose and industrial sealant, potting compound, caulk, adhesive or coating for construction use, insulated glass, structural glazing, where glass sheets are fixed and sealed in metal frame; caulks, adhesives for metal plates, car bodies, vehicles, electronic devices, and the like. Furthermore, the present composition may be used either as a one-part RTV-1 or as a two-part RTV-2 formulation that can adhere onto broad variety of metal, mineral, ceramic, rubber, or plastic surfaces.

Curable compositions comprising guanidine-containing compounds as cure accelerators may be further understood with reference to the following Examples.

EXAMPLES

Synthesis of bisguanidine (N",N'"-1,2-ethylenebis(N,N'-diisopropylguanidine))

A mixture of diisopropylcarbodiimide (8.83 g., 0.07 mol) and of ethylene diamine (2.1 g., 0.035 mol) is stirred at 40° C. for 24 hours. The GC-MS analysis shows partial conversion of reactants to desired product along with mono guanidine derivative. Subsequently, the reaction mixture is stirred at 50° C. temperature for another 24 hours. At the completion of the reaction, the formation of desired product in quantitative yield (>93%) is confirmed through GC-MS analysis. The reaction mixture is subsequently concentrated at 120° C. under 20 mbar for 2 hours, to get a yellow colored viscous material, which is found to be solidified at room temperature, indicating that the product is a low melting solid. The composition of the product was inferred through GC-MS, $^1$H NMR and $^{13}$C NMR analyses.

Synthesis of bisguanidine (N",N'"-1,2-tricyclodecanebis(N,N'-diisopropylguanidine))

A mixture of diisopropylcarbodiimide (10 g., 0.079 mol) and of tricyclodecane (TCD)-diamine (7.695 g 0.0396 mol) is stirred at 55° C. for 24 hours. As the GC-MS analysis is indicative of only a partial conversion of reactants to desired product along with the formation of mono guanidine derivatives, the reaction mixture is continued to stir at 65° C. for another 24 hours. At the completion of the reaction, the formation of desired product in quantitative yield (>91%) is confirmed by GC-MS analysis. Subsequently, the reaction mixture is concentrated at 120° C. under 20 mbar for 2 hours, to give 15.92 g (Yield 90%) of target product, as a clear colorless viscous liquid. The composition of the product is inferred through GC-MS, $^1$H NMR and $^{13}$C NMR analyses.

Measurement of Surface Curing (TFT) and Bulk Curing

The surface cure is denoted by tack free time (TFT). In a typical TFT measurement, a stainless steel (SS) weight (weighing about 10 g) is placed on the surface of the formulation spread on the Teflon mold to infer the tackiness of the surface as whether any material is adhered to the surface of the SS weight or not. TFT is defined as the time taken for getting a non-tacky surface. Bulk curing is the time taken for complete curing of formulation throughout the thickness (i.e. Top to bottom) and it is monitored as a function of time by measuring the Shore A hardness and or visual inspection.

Measurement of the Storage Stability

For aging studies the pre-mixed mixture containing crosslinker, adhesion promoter, and cure accelerator or storage stabilizer are kept in an oven for (1) 4 hours at 50° C., or (2) 5 days at 70° C., after which specified period the mixture is removed from oven and allow it to attain room temperature. The mixture is mixed with a PDMS composition using a Hauschild mixer for 1.5 min. The mixed formulation is poured into a Teflon mold (length×breadth×depth of about 10 cm×10 cm×1 cm) and placed inside a fume hood. The PDMS composition is a mixture of polydimethylsiloxane, a silica filler, The surface curing (TFT) and bulk curing is monitored as a function of time (maximum of 7 days) and °Shore A hardness in order to determine the complete cure and to what extent the compositions maintain performance after storage under accelerated conditions of cured cake (85% humidity and 85° C. An increased temperature for the storage test should simulate the storage effect at room temperature (25° C., 50% relative humidity) over longer times in a kind of time lapse.

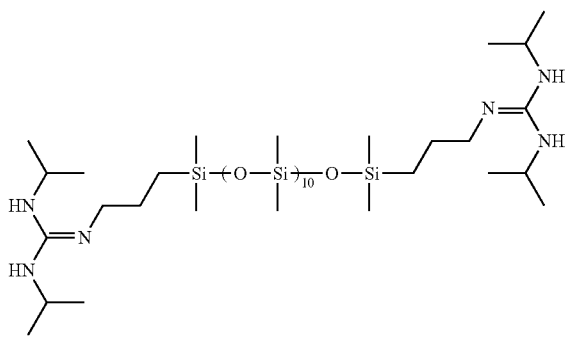 [SMILES: CC(C)NC(=NCCC[Si](C)(C)O[Si](C)(C)O[Si](C)(C)CCCN=C(NC(C)C)NC(C)C)NC(C)C]

The compositions of Examples 9-16 are shown in Table 2.

TABLE 1

| Example | PDMS (g) | X-linker (g) | Catalyst (g) | Adhesion Promoter (g) | TFT (Min) | Bulk Cure (Hrs) |
|---|---|---|---|---|---|---|
| 1 | 25 g | EPS (0.25 g) | DIC-En (0.1 g) | No AP | 4 | <15 |
| 2 | 25 g | EPS (0.25 g) | DIC-En (0.1 g) | A-1110 (0.125 g) | 5 | <15 |
| 3 | 25 g | EPS (0.25 g) | DIC-En (0.1 g) | A-1120 (0.125 g) | 5 | <15 |
| 4 | 25 g | EPS (0.25 g) | DIC-En (0.1 g) | A-1170 (0.125 g) | 3 | <15 |
| 5 | 25 g | EPS (0.25 g) | DIC-TCDDA (0.1 g) | No AP | 7 | <18 |
| 6 | 25 g | EPS (0.25 g) | DIC-TCDDA (0.1 g) | A-1110 (0.125 g) | 8 | <18 |
| 7 | 25 g | EPS (0.25 g) | DIC-TCDDA (0.1 g) | A-1120 (0.125 g) | 8 | <18 |
| 8 | 25 g | EPS (0.25 g) | DIC-TCDDA (0.1 g) | A-1170 (0.125 g) | 7 | <18 |

DIC-En: Bisguanidine derivative of N,N' diisopropylcarbodiimide and Ethylene diamine DIC-TCD-DA: Bisguanidine derivative of N,N' diisopropylcarbodiimide and TCD diimine The data in Table 1 shows that using a guanidine-containing compound can be a suitable replacement to tin as a cure accelerator or catalyst in condensation curable systems. Examples 1 and 5 show that the guanidine-containing compounds comprising a plurality of guanidine groups can provide good the curing properties even in the absence of an adhesion promoter. By using different levels of guanidine-containing-based compound and varying the adhesion promoters, the properties of the composition can be tuned or controlled for a particular purpose or intended application.

Examples 9-16 are compositions employing a bisguanidine compound that is a derivative of N,N' diisopropylcarbodiimide and an aminosiloxane fluid. The bisguanidine compound (identified as DIC-G10) is of the formula:

TABLE 2

| Example | PDMS (g) | X-linker (g) | Catalyst (g) | Adhesion Promoter (g) | TFT (Min) | Bulk Cure (Hrs) |
|---|---|---|---|---|---|---|
| 9 | 25 g | EPS (0.25 g) | DIC-G10 (0.2 g) | No AP | 20 | 24 |
| 10 | 25 g | EPS (0.25 g) | DIC-G10 (0.2 g) | A-1110 (0.125 g) | 20 | 24 |
| 11 | 25 g | EPS (0.25 g) | DIC-G10 (0.2 g) | A-1120 (0.125 g) | 17 | 24 |
| 12 | 25 g | EPS (0.25 g) | DIC-G10 (0.2 g) | A-1170 (0.125 g) | 17 | 24 |
| 13 | 25 g | EPS (0.25 g) | DIC-G10 (0.4 g) | No AP | 14 | 24 |
| 14 | 25 g | EPS (0.25 g) | DIC-G10 (0.4 g) | A-1110 (0.125 g) | 14 | 24 |
| 15 | 25 g | EPS (0.25 g) | DIC-G10 (0.4 g) | A-1120 (0.125 g) | 16 | 24 |
| 16 | 25 g | EPS (0.25 g) | DIC-G10 (0.4 g) | A-1170 (0.125 g) | 17 | 24 |

Embodiments of the invention have been described above and modifications and alterations may occur to others upon the reading and understanding of this specification. The claims as follows are intended to include all modifications and alterations insofar as they come within the scope of the claims or the equivalent thereof.

What is claimed is:

1. A composition for forming a curable polymer composition comprising:
    (A) a polymer having at least a reactive silyl group;
    (B) a crosslinker or chain extender; and
    (C) a condensation accelerator comprising a guanidine-containing compound, wherein the guanidine-containing compound comprises a plurality of guanidine functional groups, the guanidine-containing compound being chosen from a compound of the formula (i) or (ii):

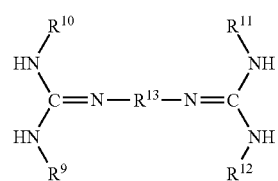

where $R^9$, $R^{10}$, $R^{11}$, and $R^{12}$ are independently chosen from an alkyl, a substituted alkyl, an alkenyl, a substituted alkenyl, an alkynyl, a substituted alkynyl, a carbocycle, a heterocycle, an aryl, or a heteroaryl; and $R^{13}$ is chosen from an alkylene, a cycloalkylene, an alkynylene, an alkenylene, an arylene, a siloxane derivative, or a polysiloxane derivative;

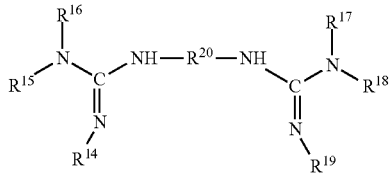

where $R^{14}$, $R^{16}$, $R^{17}$, $R^{18}$, and $R^{19}$ are independently chosen from hydrogen, an alkyl, a substituted alkyl, an alkenyl, a substituted alkenyl, an alkynyl, a substituted alkynyl, a carbocycle, a heterocycle, an aryl, or a heteroaryl; and $R^{20}$ is chosen from an alkylene, a cycloalkylene, an alkynylene, an alkenylene, an arylene, a siloxane derivative, or a polysiloxane derivative.

2. The composition of claim 1, wherein $R^9$-$R^{12}$ are individually chosen from branched or straight chain $C_1$-$C_{30}$ alkyl radical, and $R^{13}$ is chosen from a $C_1$-$C_{30}$ alkylene.

3. The composition of claim 1, wherein the guanidine-containing compound is of the formula:

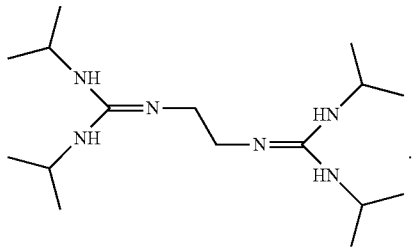 [SMILES: CC(C)NC(=NCCN=C(NC(C)C)NC(C)C)NC(C)C]

4. The composition of claim 1, wherein $R^9$-$R^{12}$ are independently chosen from a branched or straight chain $C_1$-$C_{30}$ alkyl radical, and $R^{13}$ is chosen from an alkylene comprising a carbocycle.

5. The composition of claim 4, wherein the carbocycle comprises a bridging group, a fused ring, or a fused ring system with at least one ring in the fused ring system comprising a bridging group.

6. The composition of claim 1, wherein the guanidine-containing compound is of the formula:

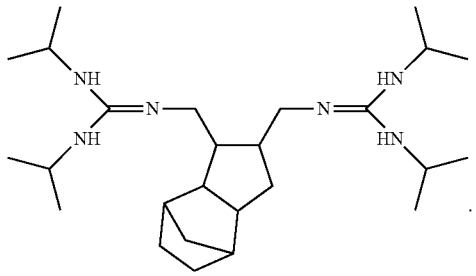 [SMILES: CC(C)NC(=NCC1CC2C3CCC(C3)C2C1CN=C(NC(C)C)NC(C)C)NC(C)C]

7. The composition of claim 1, wherein $R^{13}$ and $R^{20}$ are independently chosen from a siloxane derivative of the formula:

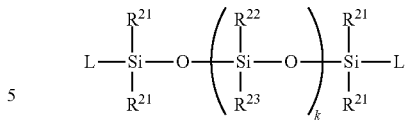

where $R^{21}$, $R^{22}$, and $R^{23}$ can be identical or different at the same silicon atom and chosen from $C_1$-$C_{10}$ alkyl; $C_1$-$C_{10}$ alkyl substituted with one or more of Cl, F, N, O, or S; a phenyl; $C_7$-$C_{16}$ alkylaryl; $C_7$-$C_{16}$ arylalkyl; $C_2$-$C_{20}$-polyalkylene ether; or a combination of two or more thereof; $R^{22}$ and $R^{23}$ can further be chosen from OH, $C_1$-$C_8$ alkoxy, $C_2$-$C_{18}$ alkoxyalkyl, alkoxyaryl, oximoalkyl, oximoaryl, enoxyalkyl, enoxyaryl, aminoalkyl, aminoaryl, carboxyalkyl, carboxyaryl, amidoalkyl, amidoaryl, carbamatoalkyl, carbamatoaryl, or a combination of two or more thereof; L is independently chosen from a bond, a divalent unit selected from the group of a $C_1$-$C_{14}$ alkylene, or O; and k is 0 to 1000.

8. The composition of claim 1, wherein the guanidine-containing compound is of the formula:

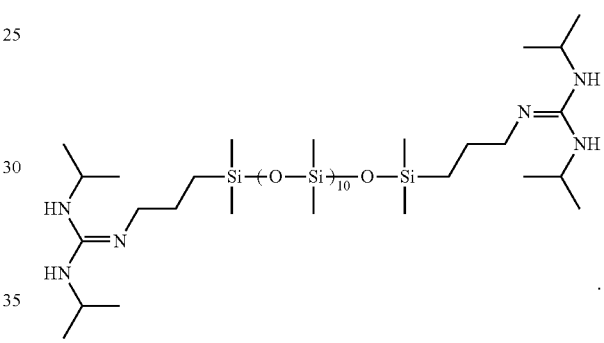

9. The composition of claim 1 comprising from about 0.0001 to about 10 parts per weight of accelerator (C) per 100 parts per weight of the polymer (A).

10. The composition of claim 1 comprising from about 0.005 to about 0.05 wt. pt. of accelerator (C) per 100 parts of the polymer (A).

11. The composition of claim 1, wherein the accelerator (C) is substantially free of tin.

12. The composition of claim 1, wherein the accelerator (C) further comprises a blend of a metal accelerator, a salt of a metal accelerator, a carboxylic acid, an alkyl-sulfonic acid, an aryl sulfonic acid, an inorganic acid, an amine, a guanidine, an amidine, an inorganic base, or a combination of two or more thereof.

13. The polymer composition of claim 1, wherein the polymer (A) has the formula (2):

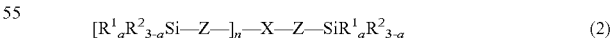

where X is chosen from a polyurethane; a polyester; a polyether; a polycarbonate; a polyolefin; a polyesterether; and a polyorganosiloxane having units of $R_3SiO_{1/2}$, $R_2SiO$, $RSiO_{3/2}$, and/or $SiO_2$; n is 0 to 100; a is 0 to 2; R and $R^1$ can be identical or different at the same Si-atom and chosen from a $C_1$-$C_{10}$ alkyl; a $C_1$-$C_{10}$ alkyl substituted with one or more of Cl, F, N, O or S; a phenyl; a $C_7$-$C_{16}$ alkylaryl; a $C_7$-$C_{16}$ arylalkyl; a $C_2$-$C_4$ polyalkylene ether; or a combination of two or more thereof; $R^2$ is chosen from OH, $C_1$-$C_8$ alkoxy, $C_2$-$C_{18}$ alkoxyalkyl, oximoalkyl, enoxyalkyl, aminoalkyl, carboxyalkyl, amidoalkyl, amidoaryl, carbamatoalkyl, or a combination of two or more thereof; and Z is a bond, a divalent unit selected from the group of a $C_1$-$C_8$ alkylene, or O.

14. The polymer composition of claim 1, wherein the polymer component (A) has the formula (4):

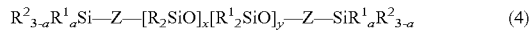

$$R^2{}_{3-a}R^1{}_aSi-Z-[R_2SiO]_x[R^1{}_2SiO]_y-Z-SiR^1{}_aR^2{}_{3-a} \quad (4)$$

where x is 0 to 10000; y is 0 to 1000; a is 0 to 2; R is methyl; $R^1$ is chosen from a $C_1$-$C_{10}$ alkyl; a $C_1$-$C_{10}$ alkyl substituted with one or more of Cl, F, N, O, or S; a phenyl; a $C_7$-$C_{16}$ alkylaryl; a $C_7$-$C_{16}$ arylalkyl; a $C_2$-$C_4$ polyalkylene ether; or a combination of two or more thereof, and other siloxane units may be present in amounts less than 10 mol. % preferably methyl, vinyl, phenyl; $R^2$ is chosen from OH, a $C_1$-$C_8$ alkoxy, a $C_2$-$C_{18}$ alkoxyalkyl, an oximoalkyl, an oximoaryl, an enoxyalkyl, an enoxyaryl, an aminoalkyl, an aminoaryl, a carboxyalkyl, a carboxyaryl, an amidoalkyl, an amidoaryl, a carbamatoalkyl, a carbamatoaryl, or a combination of two or more thereof; and Z is —O—, a bond, or —$C_2H_4$—.

15. The composition of claim 1, wherein the polymer (A) is chosen from silylated polyurethane (SPUR), silylated polyester, silylated polyether, silylated polycarbonate, silylated polyolefins like polyethylene, polypropylene, silylated polyesterether and combinations of two or more thereof.

16. The composition of claim 1, wherein the crosslinker (B) is chosen from an alkoxysilane, an alkoxysiloxane, an oximosilane, an oximosiloxane, an enoxysilane, an enoxysiloxane, an aminosilane, an aminosiloxane, a carboxysilane, a carboxysiloxane, an alkylamidosilane, an alkylamidosiloxane, an arylamidosilane, an arylamidosiloxane, an alkoxyaminosilane, an alklarylaminosiloxane, an alkoxycarbamatosilane, an alkoxycarbamatosiloxane, a hydridosilane, a hydridosiloxane, and combinations of two or more thereof.

17. The composition of claim 1 wherein the crosslinker component (B) is chosen from tetraethylorthosilicate (TEOS); methyltrimethoxysilane (MTMS); methyltriethoxysilane; vinyltrimethoxysilane; vinyltriethoxysilane; methylphenyldimethoxysilane; 3,3,3-trifluoropropyltrimethoxysilane; methyltriacetoxysilane; vinyltriacetoxysilane; ethyltriacetoxysilane; di-butoxydiacetoxysilane; phenyltripropionoxysilane; methyltris(methylethylketoximo)silane; vinyltris(methylethylketoximo)silane; 3,3,3-trifluoropropyltris(methylethylketoximo)silane; methyltris(isopropenoxy) silane; vinyltris(isopropenoxy)silane; ethylpolysilicate; dimethyltetraacetoxydisiloxane; tetra-n-propylorthosilicate; methyldimethoxy(ethylmethylketoximo)silane; methylmethoxybis(ethylmethylketoximo)silane; methyldimethoxy (acetaldoximo)silane; methyldimethoxy(N-methylcarbamato)silane; ethyldimethoxy(N-methylcarbamato)silane; methyldimethoxyisopropenoxysilane; trimethoxyisopropenoxysilane; methyltriisopropenoxysilane; methyldimethoxy (but-2-en-2-oxy)silane; methyldimethoxy(1-phenylethenoxy)silane; methyldimethoxy-2-(1-carboethoxypropenoxy)silane; methylmethoxydi(N-methylamino)silane; vinyldimethoxy(methylamino)silane; tetra-N,N-diethylaminosilane; methyldimethoxy(methylamino)silane; methyltri(cyclohexylamino)silane; methyldimethoxy(ethylamino)silane; dimethyldi(N,N-dimethylamino) silane; methyldimethoxy(isopropylamino)silane; dimethyldi (N,N-diethylamino)silane; ethyldimethoxy(N-ethylpropionamido)silane; methyldimethoxy(N-methylacetamido)silane; methyltris(N-methylacetamido) silane; ethyldimethoxy(N-methylacetamido)silane; methyltris(N-methylbenzamido)silane; methylmethoxybis (N-methylacetamido)silane; methyldimethoxy(caprolactamo)silane; trimethoxy(N-methylacetamido)silane; methyldimethoxy(ethylacetimidato)silane; methyldimethoxy(propylacetimidato)silane; methyldimethoxy(N,N',N'-trimethylureido)silane; methyldimethoxy(N-allyl-N',N'-dimethylureido)silane; methyldimethoxy(N-phenyl-N',N'-dimethylureido)silane; methyldimethoxyisocyanatosilane; dimethoxydiisocyanatosilane; methyldimethoxyisothiocyanatosilane; methylmethoxydiisothiocyanatosilane, the condensates thereof, a hydridosilane, a hydridosiloxane, or a combination of two or more thereof.

18. The composition of claim 1, wherein the composition is free of an adhesion promoter.

19. The composition of claim 1 comprising an adhesion promoter component (D).

20. The composition of claim 19, wherein the adhesion promoter is chosen from an (aminoalkyl)trialkoxysilane, an (aminoalkyl)alkyldialkoxysilane, a bis(trialkoxysilylalkyl) amine, a tris(trialkoxysilylalkyl)amine, a tris(trialkoxysilylalkyl)cyanurate, a tris(trialkoxysilylalkyl)isocyanurate, an (epoxyalkyl)alkyldialkoxysilane, an (epoxyalkyl)trialkoxysilane, or a combination of two or more thereof.

21. The composition of claim 1 comprising a filler component (E).

22. The composition of claim 1 comprising at least one acidic compound (F) chosen from a phosphate ester, a phosphonate ester, a phosphonic acid, a phosphorous acid, a phosphite, a phosphonite ester, a sulfate, a sulfite, a pseudohalogenide, a branched $C_4$-$C_{25}$ alkyl carboxylic acid, or a combination of two or more thereof.

23. The composition of claim 1, wherein the composition is a two-part composition comprising: (i) a first portion comprising the polymer component (A), optionally a filler component (E), and optionally an acidic compound (F); and (ii) a second portion comprising the crosslinker (B), the accelerator (C), optionally an adhesion promoter (D), and the acidic compound (F), whereby (i) and (ii) are stored separately until applied for curing by mixing of the components (i) and (ii).

24. A cured polymer formed from the composition of claim 1.

25. The cured polymer of claim 24 in the form of an elastomeric seal, duromeric seal, an adhesive, a coating, an encapsulant, a shaped article, a mold, or an impression material.

26. The cured polymer material of claim 24, wherein the polymer is formed by crosslinking via a condensation reaction and/or a dehydrogenative condensation reaction.

27. The composition of claim 1, wherein $R^9$-$R^{12}$ and $R^{14}$-$R^{19}$ are independently chosen from a substituted or unsubstituted, branched or straight chain $C_1$-$C_{30}$ alkyl; a substituted or unsubstituted, branched or straight chain $C_2$-$C_{18}$ alkenyl; a substituted or unsubstituted, branched or straight chain $C_2$-$C_{18}$ alkynyl; —$(OCH_2CH_2)_{1-15}OH$; —$(OC_3H_6)_{1-15}OH$; a substituted or unsubstituted, saturated or unsaturated, carbocycle or heterocycle; or a substituted or unsubstituted aryl or heteroaryl.

28. The composition of claim 1, wherein $R^9$-$R^{12}$ and $R^{14}$-$R^{19}$ are independently chosen from a substituted or unsubstituted, branched or straight chain $C_1$-$C_9$ alkyl; a substituted or unsubstituted, branched or straight chain $C_2$-$C_9$ alkenyl; a substituted or unsubstituted, branched or straight chain $C_2$-$C_9$ alkynyl; substituted or unsubstituted, saturated or unsaturated, carbocycles or heterocycles; or substituted or unsubstituted aryl or heteroaryl.

29. The composition of claim 1, wherein $R^9$-$R^{12}$ and $R^{14}$-$R^{19}$ are independently chosen from substituted or unsubstituted, branched or straight chain $C_1$-$C_5$ alkyl; substituted or unsubstituted, branched or straight chain $C_2$-$C_5$ alkenyl; substituted or unsubstituted, branched or straight chain $C_2$-$C_5$ alkynyl; substituted or unsubstituted, saturated or unsaturated, carbocycle or heterocycle selected from cyclopropyl, cyclobutyl, cyclopentyl, cyclohexyl, pyrrolidinyl, piperidyl, imidazolidinyl, pyrazolidinyl, pyrazolinyl, piperazinyl, morpholinyl, chromanyl, and indolinyl, including their corresponding iso-forms; or a substituted or unsubstituted fused or unfused aryl or heteroaryl selected from phenyl, benzyl, naphthyl, furyl, benzofuranyl, pyranyl, pyrazinyl, thienyl, pyrrolyl, imidazolyl, pyridyl, pyrimidinyl, pyridazinyl, indolyl, indolizinyl, indoazolyl, purinyl, quinolyl, thiazolyl, phthalazinyl, quinoxalinyl, quinazolinyl, benzothienyl, anthryl, and phenathtryl, including their corresponding iso-forms.

30. The composition of claim 1, wherein $R^9$-$R^{12}$ and $R^{14}$-$R^{19}$ are independently chosen from are methyl, ethyl, propyl, isopropyl, butyl, isobutyl, tert-butyl, 2-ethyl-hexyl, cyclopentyl, cyclohexyl, phenyl, pyridinyl, or pyrrolidinyl.

31. The composition of claim 1, wherein $R^{13}$ and $R^{20}$ are independently chosen from an alkylene group having 1 to 30 carbon atoms, an aralkylene group having 7 to 30 carbon atoms, or an arylene group having 6 to 30 carbon atoms.

32. The composition of claim 1, wherein $R^{13}$ and $R^{20}$ are independently chosen from an alkylene group having 1 to 12 carbon atoms, an aralkylene group having even 7 to 13 carbon atoms, or an arylene group having 6 to 15 carbon atoms.

* * * * *